United States Patent
Spence et al.

(10) Patent No.: US 6,488,692 B1
(45) Date of Patent: Dec. 3, 2002

(54) ACCESS AND CANNULATION DEVICE AND METHOD FOR RAPIDLY PLACING SAME AND FOR RAPIDLY CLOSING SAME IN MINIMALLY INVASIVE SURGERY

(75) Inventors: Paul A. Spence, Louisville, KY (US); Warren P. Williamson, IV, Loveland, OH (US); George Christakis, Toronto (CA)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/520,468

(22) Filed: Mar. 7, 2000

Related U.S. Application Data

(60) Continuation-in-part of application No. 09/200,796, filed on Nov. 27, 1998, now Pat. No. 6,254,617, which is a division of application No. 08/714,615, filed on Sep. 16, 1996, now Pat. No. 5,868,763.
(60) Provisional application No. 06/136,427, filed on May 28, 1999.

(51) Int. Cl.[7] .............................................. A61B 17/04
(52) U.S. Cl. ..................................... 606/153; 606/139
(58) Field of Search ............................. 606/153, 139, 606/154, 155

(56) References Cited

U.S. PATENT DOCUMENTS

| | | | |
|---|---|---|---|
| 3,155,095 A | 11/1964 | Brown ........................ 128/334 |
| 3,166,072 A | 1/1965 | Sullivan, Jr. |
| 3,254,650 A | 6/1966 | Collito |
| 3,258,012 A | 6/1966 | Nakayama et al. |
| 3,606,888 A | 9/1971 | Wilkinson |
| 3,657,744 A | 4/1972 | Ersek ............................... 3/1 |
| 3,683,926 A | 8/1972 | Suzuki ........................ 606/153 |
| 3,774,615 A | 11/1973 | Lim et al. |
| 3,908,662 A | 9/1975 | Razgulov et al. |
| 3,938,528 A | 2/1976 | Bucalo ........................ 128/334 |
| 3,973,570 A | 8/1976 | Razgulov et al. ............ 128/337 |
| 3,974,835 A | 8/1976 | Hardy, Jr. |
| 3,993,078 A | 11/1976 | Bergentz et al. ............. 128/334 |
| 4,055,186 A | 10/1977 | Leveen ........................ 128/334 |
| 4,214,586 A | 7/1980 | Mericle |

(List continued on next page.)

FOREIGN PATENT DOCUMENTS

| | | |
|---|---|---|
| DE | 2822603 A1 | 11/1979 |
| DE | 28 22 603 A1 | 11/1979 |
| DE | 297 13 335 U1 | 11/1997 |

(List continued on next page.)

OTHER PUBLICATIONS

C.A.F. Tulleken et al., "End–to–end anastomosis of small vessels using an ND:YAG laser with a hemispherical contact probe", Technical Note, J. Neurosurg., vol. 76, Mar. 1992, pp. 546–549.

(List continued on next page.)

*Primary Examiner*—Gary Jackson
(74) *Attorney, Agent, or Firm*—Thelen Reid & Priest LLP

(57) ABSTRACT

An access and cannulation device includes a mounting element such as the anastomosis mounting element disclosed in U.S. application Ser. No. 08/714,615 (now U.S. Pat. No. 5,868,763) and U.S. application Ser. No. 09/200,796. The device is used to provide access therethrough and via an incision to the interior of a hollow anatomical structure such as a vessel, an organ or the like during surgery, especially minimally invasive surgery. It includes a flexible sleeve with a suture therein for closing the sleeve and locating edges of the structure adjacent to the incision in position for proper healing after completion of a surgical procedure. A tool is also disclosed for manipulating the device to configure it for the surgery and to close it after completion of the surgery whereby the edges of the wall of the structure adjacent to an incision are approximated to promote proper healing.

60 Claims, 20 Drawing Sheets

U.S. PATENT DOCUMENTS

| | | |
|---|---|---|
| 4,214,587 A | 7/1980 | Sakura |
| 4,233,981 A | 11/1980 | Schomacher |
| 4,345,600 A | 8/1982 | Rothfuss .................... 128/334 |
| 4,368,736 A | 1/1983 | Kaster ........................ 128/334 |
| 4,474,181 A | 10/1984 | Schenck |
| 4,523,592 A | 6/1985 | Daniel |
| 4,657,019 A | 4/1987 | Walsh et al. |
| 4,676,245 A | 6/1987 | Fukuda |
| 4,681,110 A | 7/1987 | Wiktor ...................... 128/343 |
| 4,747,407 A | 5/1988 | Liu et al. |
| 4,787,386 A | 11/1988 | Walsh et al. ................ 128/334 |
| 4,872,874 A | 10/1989 | Taheri ........................... 623/1 |
| 4,873,975 A | 10/1989 | Walsh et al. |
| 4,899,744 A | 2/1990 | Fujitsuka et al. |
| 4,930,502 A | 6/1990 | Chen |
| 4,930,674 A | 6/1990 | Barak ........................ 227/179 |
| 4,950,283 A | 8/1990 | Dzubow et al. ............ 606/216 |
| 4,957,499 A | 9/1990 | Lipatov et al. ............. 606/153 |
| 4,979,954 A | 12/1990 | Gwathmey et al. ......... 606/219 |
| 4,997,439 A | 3/1991 | Chen |
| 5,035,702 A | 7/1991 | Taheri ........................ 606/153 |
| 5,037,428 A | 8/1991 | Picha et al. |
| 5,078,735 A | 1/1992 | Mobin-Uddin ................ 623/1 |
| 5,089,008 A | 2/1992 | Chen |
| 5,123,908 A | 6/1992 | Chen |
| 5,188,638 A | 2/1993 | Tzakis |
| 5,234,447 A | 8/1993 | Kaster et al. |
| 5,250,057 A | 10/1993 | Chen |
| 5,263,973 A | 11/1993 | Cook |
| 5,336,233 A | 8/1994 | Chen |
| 5,366,462 A | 11/1994 | Kaster et al. ............... 606/153 |
| 5,403,333 A | 4/1995 | Kaster et al. ............... 606/153 |
| 5,486,187 A | 1/1996 | Schenck |
| 5,501,689 A | 3/1996 | Green et al. ................ 606/139 |
| 5,562,690 A | 10/1996 | Green et al. ................ 606/154 |
| 5,653,743 A | 8/1997 | Martin ....................... 606/153 |
| 5,683,453 A | 11/1997 | Palmaz ...................... 606/153 |
| 5,695,504 A | 12/1997 | Gifford, III et al. ......... 606/153 |
| 5,702,048 A | 12/1997 | Eberlin ....................... 227/177 |
| 5,707,380 A | 1/1998 | Hinchliffe et al. .......... 606/153 |
| 5,741,274 A | 4/1998 | Lenker et al. .............. 606/142 |
| 5,752,966 A | 5/1998 | Chang ....................... 606/151 |
| 5,879,371 A | 3/1999 | Gardiner et al. ............ 606/224 |
| 5,904,697 A | 5/1999 | Gifford, III et al. ......... 606/155 |
| 5,938,696 A | 8/1999 | Goicoechea et al. ........... 623/1 |
| 5,957,973 A | 9/1999 | Quiachon et al. .............. 623/1 |
| 5,976,159 A | 11/1999 | Bolduc et al. .............. 606/142 |
| 5,976,178 A | 11/1999 | Goldsteen et al. ............. 623/1 |
| 6,068,637 A | 5/2000 | Popov et al. ............... 606/159 |

FOREIGN PATENT DOCUMENTS

| | | |
|---|---|---|
| EP | 0539237 A1 | 4/1993 |
| GB | 1181563 | 2/1967 |
| WO | WO 95/17127 | 6/1995 |
| WO | WO 95/17128 | 6/1995 |
| WO | WO 95/35065 | 12/1995 |
| WO | WO 98/02099 | 1/1998 |
| WO | WO 98/19630 | 5/1998 |
| WO | WO 99/21491 | 5/1999 |

OTHER PUBLICATIONS

Robin H. Heijmen, M.D., et al. "A Novel One–Shot Anastomotic Stapler Prototype for Coronary Bypass Grafting on the Beating Heart: Feasbility in the Pig", Journal of Thoracic and Cardiovascular Surgery, Jan. 1999, pp. 117–125.

SECTION B-B

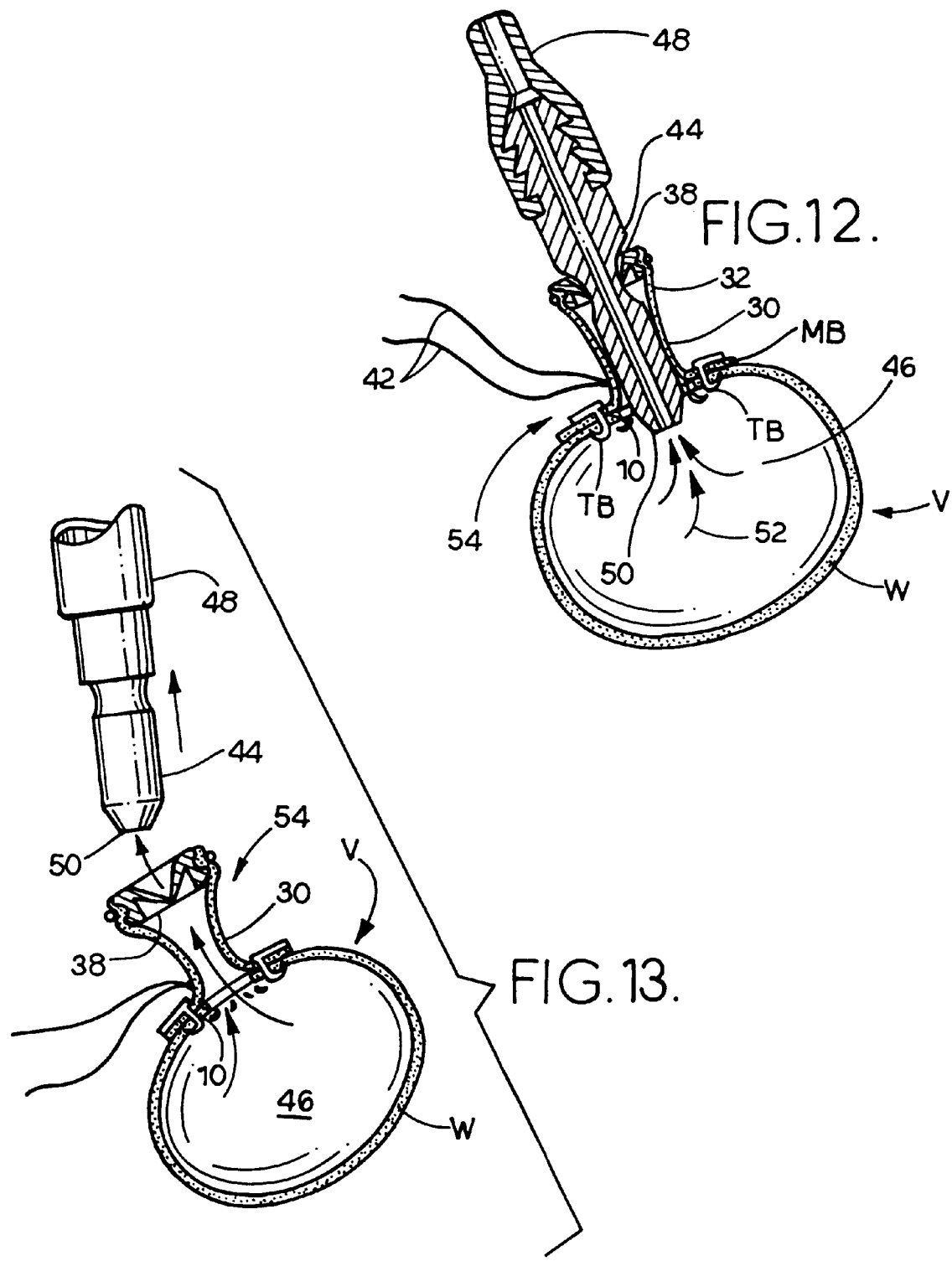

FIG. 21.
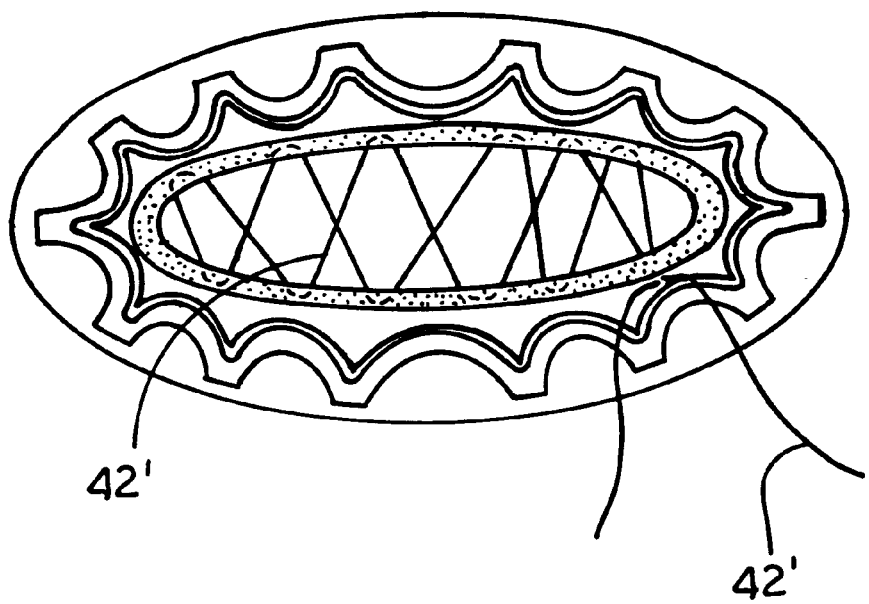
42'  42'
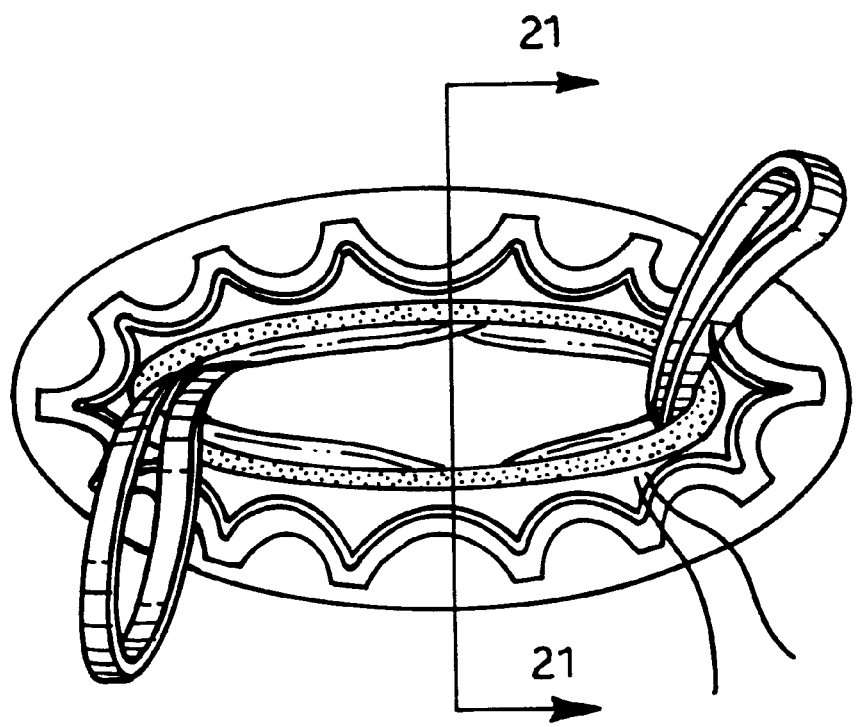
FIG. 22.

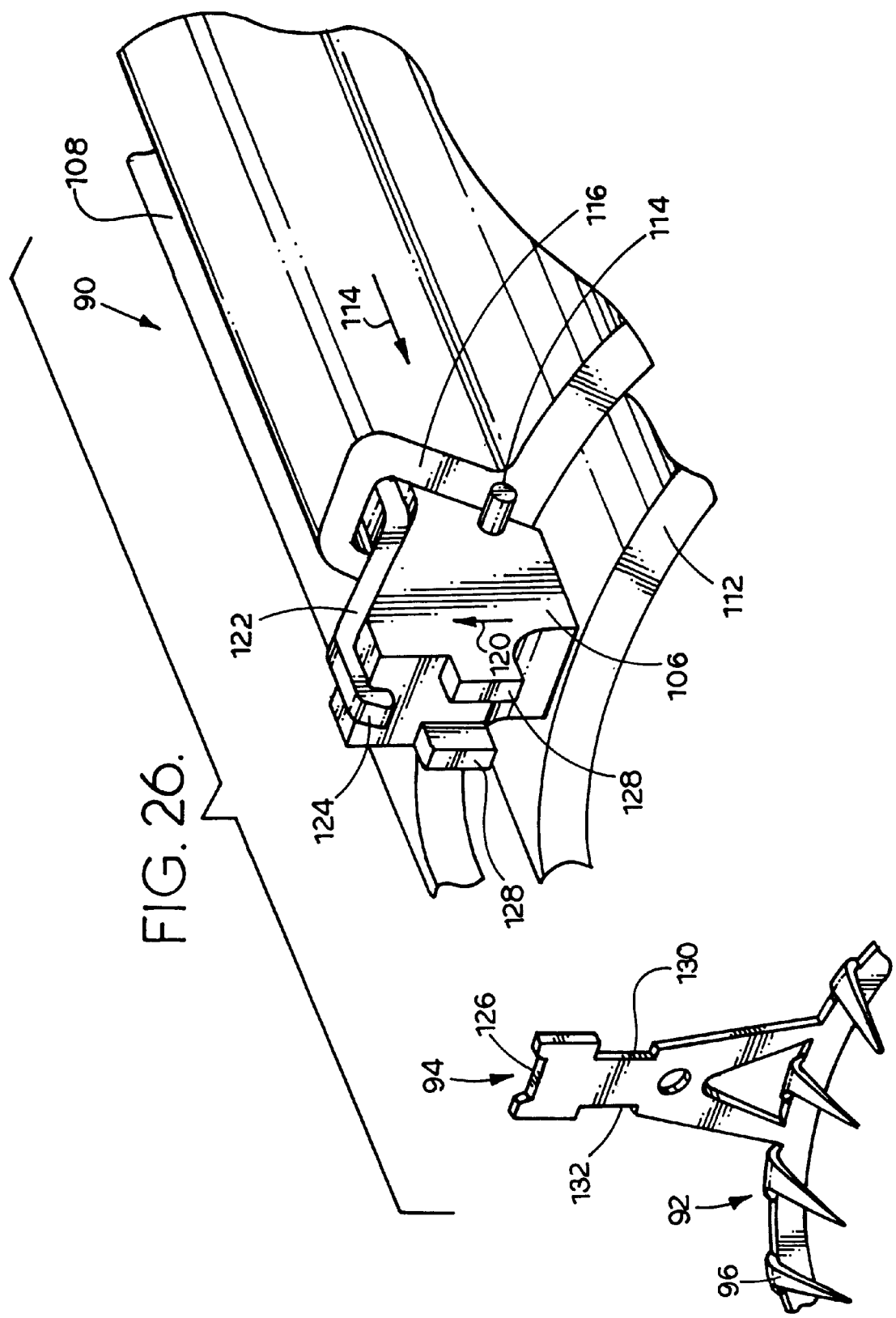

ACCESS AND CANNULATION DEVICE AND METHOD FOR RAPIDLY PLACING SAME AND FOR RAPIDLY CLOSING SAME IN MINIMALLY INVASIVE SURGERY

CROSS-REFERENCE TO RELATED APPLICATIONS

This application claims benefit of Provisional Application No. 60/136,427 filed May 28, 1999.

The present application is a continuation-in-part of application Ser. No. 09/200,796 filed on Nov. 27, 1998 now U.S. Pat. No. 6,254,617, which is a division of application Ser. No. 08/714,615 filed on Sep. 16, 1996, now U.S. Pat. No. 5,868,763. The disclosures of said prior applications are fully incorporated herein by reference.

TECHNICAL FIELD OF THE INVENTION

The present invention relates to the general art of surgery, and to the particular field of minimally invasive surgery.

BACKGROUND OF THE INVENTION

As discussed in the incorporated documents, there is current interest in surgical techniques that are less invasive than previous techniques. This current interest has engendered interest in many areas that were previously abandoned including coronary fastening and valve placement among other areas that will occur to those skilled in the surgical art.

Furthermore, many of these procedures include use of cardiopulmonary bypass for their execution. Cardiopulmonary bypass removes the venous blood from the heart and returns it to the circulation system of the patient through the patient's aorta or through one of its branches after it has been oxygenated. This bypass procedure makes it possible to remove the heart from the circulation system in order to perform corrections on the heart and also makes it possible to arrest the heart so that there is a non-moving field that is relatively free of obstructions for the surgeon to work.

Numerous surgical procedures such as the just-mentioned cardiopulmonary bypass procedures require cannulation of a hollow anatomical structure such as the heart, the great vessels associated with the heart as well as other internal organs during the course of surgical procedures. Venous cannulation (where unoxygenated blood is removed from the patient's circulation system) can be performed in the right atrium, SVC, IVC or other major venous branch. Typically, blood is removed from the right atrium by cannulas which have extensions into the SVC or IVC. A single cannula is sufficient for routine bypass procedures. Such a cannula typically has a basket-shaped area which sits in the right atrium and has an extension into the IVC. For valve procedures or in situations where it is necessary to totally exclude blood from the heart, it is necessary to drain blood from both the SVC and the IVC independently so that two cannulation sites and two cannulas are required.

Oxygenated blood is usually returned via the aorta (arterial cannulation site). This is usually accomplished with a single cannula of smaller diameter than the venous cannula since blood is pumped into the patient. The pumped blood distributes itself in the arterial system.

Cannulation sites are also necessary for other purposes. Cardioprotective solutions (cardioplegia) are often infused into the coronary arteries through the aortic root. Such solutions can also be delivered into the coronary sinus and used to perfuse the myocardium in a reverse direction (i.e., vein to myocardium to artery), which is also known as "retrograde cardioplegia." Cannulation is also necessary when pressure or flow monitoring catheters are introduced into the heart or great vessels.

In short, cannulation is an essential component of many surgery procedures associated with a hollow anatomical structure such as the heart or blood vessels. Therefore, there is a need for efficient and effective means and methods for carrying out cannulation during a surgical procedure associated with a hollow anatomical structure and whenever cardiopulmonary bypass is necessary or whenever catheters or tubes must be inserted into the heart. This is especially so during minimally invasive surgery.

Many operations still require a considerable incision or port to conduct the operation, and many of these operations require hand suturing to perform the procedures. Smaller access sites must be used to effect truly minimally invasive procedures on patients. This necessitates technologies which obviate the need for suturing and other fine motor tasks which require direct visualization and hand suturing since the suturing will be difficult with the limited access associated with minimally invasive surgery.

Still further, general access restrictions make manipulations difficult and blood in the surgical field is also a cause for concern. Therefore, there is a need for providing a generally bloodless field when carrying out the steps associated with cannulation and subsequent closure of the cannulation incision. Furthermore, blood leakage may cause a problem. Therefore, there is a need for a cannulation means and method which can be carried out in minimally invasive surgery and which will minimize, if not totally eliminate, blood in the surgical field.

Since cannulation is an area which has heretofore required considerable hand suturing, there is a need for a cannulation device and method which requires only a minimal incision in the patient and eliminates the need for hand suturing. The device and any tools associated therewith could, for example, allow the cannulation of the heart by a tiny incision or port because no hand suturing would be necessary. During such a procedure, the patient could be placed on bypass by cannulas in the heart without the need for large incisions. Other examples of such nonhand sutured cannulation include procedures on any hollow anatomical structure, including blood vessels and other organs as will be known to those skilled in the medical art.

In addition to hand suturing techniques required by the prior art, the prior art discloses devices which incorporate a variety of balloon configurations which act to seal an incision site while cannulas are in place and which can also restrict the flow of blood to and through the structure, such as a major vessel. One problem with such devices is caused when the cannula is removed and the only way to re-establish patency of the vessels is to hand suture them closed. This method is not well suited to the small incisions used in minimally invasive surgery since hand suturing requires more room to manipulate tools and also to enable the surgeon to visualize what he or she is doing. Therefore, in addition to the needs discussed above, there is also a need for a device which can be placed in a patient without requiring hand suturing and which is suitable for use in minimally invasive surgery to meet these requirements as well.

In addition, older patients may have frail tissue which result in trouble pulling purse-string sutures tight. In some cases, the sutures will cut the tissue causing further leaks which must be patched and sutured again. Therefore, there is a need for a means and a method for setting a cannula in a patient who may have fragile and/or friable tissue, especially in minimally invasive surgery.

It is also noted that anchoring a cannula in tissue stresses that tissue by transmitting any forces associated with the cannula or movements of the cannula to the tissue. As is especially the case with frail tissue, such anchoring may tend to tear the tissue. Therefore, there is a need for a means and a method for attaching a cannula to an anatomical structure in a manner that reduces or eliminates cannula-induced stress on the tissue.

Closure of purse-string sutures causes the tissue to be gathered and bunched resulting in a loss of cross-sectional area and/or a decreased function. Therefore, there is a need for a means and a method for gaining access to the interior of an organ or a vessel that can be closed without causing bunching and/or gathering of the patient's tissue.

Still further, in manually sutured procedures a substantial amount of tissue is required to make a port closure. For example, when the atrium of the heart or the aorta is cannulated with a purse-string suture the tissue inside the purse string is lost when the suture is tied. This causes stretching and deformity of the heart or aorta when the purse-string is tied, sometimes leading to tears in the tissue and/or leaks. Therefore, there is a need for a means and a method for cannulating organs which does not require purse-string sutures.

Specifically, surgeries on many organs also require opening the organ and/or the vessels associated with therewith. The vessels must be closed at the end of the procedure to complete the operation. It is important to minimally invasive procedures to have a tool which will allow closure of such organs and vessels without the need of hand suturing.

For example, the replacement of the aortic valve requires cannulation of the aorta and the right atrium for the commencement of cardiopulmonary bypass. The aorta is then opened above the aortic valve and the defective valve is removed and then replaced. The aorta must then be closed hemostatically and the cardiopulmonary bypass pump discontinued followed by removal of the cannulas from the heart. In order for this procedure to be performed through truly tiny apertures in the patient, there is a need for a means and method for mechanically opening and closing the aorta.

As can be understood from the above discussion, a device which opens an organ or other such structure and allows it to be closed by a simple tightening of a suture without the need for placement of hand-placed stitches is needed. The device should take into account that many patients have weak and friable tissue. Often when a structure such as a great vessel is closed with sutures the tissue wall tears at the sutures. The prior art deals with this problem by applying surgical felt to the leaky areas. However, the felt is secured with sutures and more holes and tearing can occur at the patch site. Therefore, it is desirable to have a closure device and method which will reinforce frail tissue and reduce tears.

High doses of anticoagulants are usually administered to patients undergoing heart surgery, such as cardiopulmonary bypass, to prevent blood clots during the surgery. These drugs prevent the clotting process from starting in the centrifugal extracorporeal pump circuit. However, these same drugs make it difficult to get large incisions in the vessel walls and heart muscle or other internal organs to seal. Therefore, there is a need to provide a hemostatic medium which is held in the proximity of a wound to prevent blood loss until the patient's natural clotting cycle can seal the wound. In addition, a mechanical means to hold the organ or vessel walls in tight approximation is needed to ensure stability and security of wound closure.

As discussed above some procedures require multiple access sites. In such situations sealing the tissue to the cannulation incision is very difficult. Often, two separate sites are required. In some instances multiple access sites will multiply the above-discussed problems. Therefore, there is a need for a means and a method for providing multiple access sites to internal organs which can be effectively and efficiently sealed.

OBJECTS OF THE INVENTION

It is a main object of the present invention to provide a leak-free method of cannulating of an internal organ.

It is another object of the present invention to provide a leak-free method of cannulating a vessel.

It is another object of the present invention to provide a unique docking mechanism for a bypass cannula.

It is another object of the present invention to provide an apparatus and method for cannulation which can reinforce the tissue to which the cannula is attached.

It is another object of the present invention to provide an apparatus and method for quickly closing a cannula incision in great vessels, organs or ventricles.

It is another object of the present invention to provide an apparatus and method to cannulate vessels in minimally invasive surgery with small access restrictions.

It is another object of the present invention to obviate the need to suture within a narrow minimally invasive access site.

It is another object of the present invention to provide a cannulation port which closes the port wound with a minimum amount of bunching or gathering of tissue.

It is another object of the present invention to prevent loss of atrium or vessel size on closure of a cannulation site.

It is another object of the present invention to minimize leaks on closure of a cannulation port.

It is another object of the present invention to provide an apparatus and method for sealing an incision instrument against a valve used in cannulating the patient as the cannulation port is being defined.

It is another object of the present invention to provide a single access port which can accommodate more than one cannula without leakage.

It is another object of the present invention to provide an apparatus and method for purging air from the cannulation port.

It is another object of the present invention to allow closure of a cannulation site after it is needed by simply drawing up one suture.

It is another object of the present invention to provide an apparatus and method for gaining access to vessels in minimally invasive surgery within small access restrictions.

It is another object of the present invention to provide an apparatus and method for gaining leak-free access to and closure of great vessels of the heart and other anatomical structures without placing sutures in the anatomical structure.

It is another object of the present invention to prevent loss of atrium or vessel size or volume on closure of a cannulation access device.

It is another object of the present invention to provide an access and closure port for an internal vessel or structure that provides a minimum amount of bunching or gathering of tissue on closure.

It is another object of the present invention to provide a cannulation access device with a malleable frame which holds the incision open when desired.

It is another object of the present invention to provide a cannulation access apparatus and method which can reinforce the tissue to which it is attached with a mechanical fastener.

It is another object of the present invention to provide an access and cannulation and closure device that approximates the edges of the tissue to which it is attached to improve healing.

It is another object of the present invention to provide an access and closure device which includes a hemostatic medium to promote healing of the incision.

It is another object of the present invention to provide a built-in closure means to allow simple closure of the access site with a minimum of effort.

It is another object of the present invention to provide an apparatus for providing access to the interior of an anatomical structure that will act as a stress relief element and will isolate an instrument, such as a cannula, from the tissue whereby instrument-induced forces will not be transferred to the tissue.

SUMMARY OF THE INVENTION

These, and other, objects are achieved by a device for establishing restricted access to a hollow anatomical structure such as a vessel, a heart or any internal organ of a patient during surgery. One embodiment includes a flexible sleeve and a malleable frame that is mounted on the wall of the structure adjacent to an incision in the wall of the structure and a one-way port on the sleeve through which a cannula is inserted to access the interior of the anatomical structure, and a suture on the sleeve for closing the sleeve and approximating the tissue adjacent to the incision into a healing position after completion of the procedure.

Incorporated applications Ser. Nos. 08/714,615 and 09/200,796 describe a mechanical fastening device used for coronary vessel anastomosis. Another embodiment employs such a fastening device and includes a malleable anchor ring with a multiplicity of tines that attach to the vessel or organ. The ring has a material memory such that once deformed it remains in the deformed configuration until physically moved to another configuration. This ring is easily mounted on a vessel or other organ adjacent to an incision and is easily deformed to open or close the incision as desired. The present invention utilizes this malleable ring as an anchor element for a cannulation port.

The cannulation device of the present invention can be placed and configured on the vessel or organ during minimally invasive surgery, and can be closed after use from outside the patient. By selecting from a plurality of different sleeves, the type of access and cannulation can be easily selected. For example, single or multiple cannulas can be accommodated by the device of the present invention.

Because the device is easily set and closed small sites can be accommodated, and virtually no blood will seep into the surgical field. Furthermore, since no hand suturing is required to close the site all of the above-discussed problems associated with suturing and hand suturing in particular, are eliminated. The mounting tines of the mounting ring anchor the ring in a manner that will not endanger tissue, especially fragile tissue, and thereby will reduce or eliminate the problems associated with damaging tissue due to placing and sealing an access port. The sleeve is flexible and isolates the cannula from the malleable ring and thus relieves stress that otherwise might be transferred from the cannula to the tissue.

Because of the secure nature of the mounting, leaks are virtually non-existent, even in fragile tissue.

BRIEF DESCRIPTION OF THE DRAWING FIGURES

Other objects, features and advantages of the invention will become apparent from a consideration of the following detailed description and the accompanying drawings.

FIG. 12 shows a cross-sectional view of the cannula tip in place in a great vessel.

FIG. 13 shows the cannula tip removed and the valve closed preventing leaks.

FIG. 21 shows a top view of the access and closure port with drawstrings for closure being shown for clarity.

FIG. 22 is a top view of the access and closure port showing the closure sutures being drawn to each side and being held in place with a bulldog-type clip.

FIG. 26 is a perspective view showing the tool in combination with the ring of the device.

DETAILED DESCRIPTION OF THE PREFERRED EMBODIMENTS OF THE INVENTION

By way of background, the prior art method of cannulating a vessel will be described so the present invention will be appreciated. Referring to FIGS. 1–5, it can be understood that current surgical procedures employ a purse-string suture to tighten the tissue around a cannula tip. The procedure will be described below.

An incision I will be made in the wall of a vessel V. Before incision I is made, a running monofilament or braided suture S is made in a circle around an area that is approximately one to three cm in diameter. Ends E of sutures S are then fed through a piece of tubing T which is used as a garrote. Incision I is then made in the center of the circle of the stitches and the tip of cannula CN is inserted through the incision into the interior or vessel V.

The purse-string sutures are then pulled up tight while pushing down on tube T so the tissue is gathered and tightened down on cannula CN adjacent to the tip thereof. A hemostat H is then clamped onto the tube T which in turn clamps around suture S in the bore of the tube to hold the sutures tight without having to put a knot in the sutures.

Figure 1:
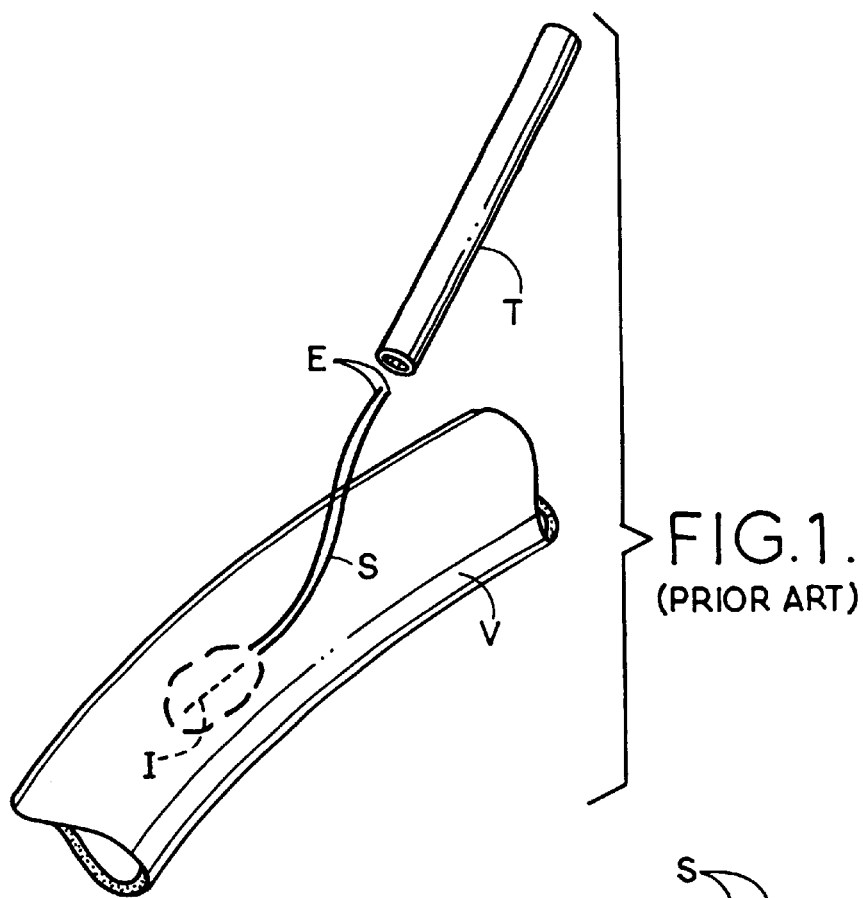
FIG. 1 shows a prior art method of preparing a purse-stringed cannula port.
Figure 2A:
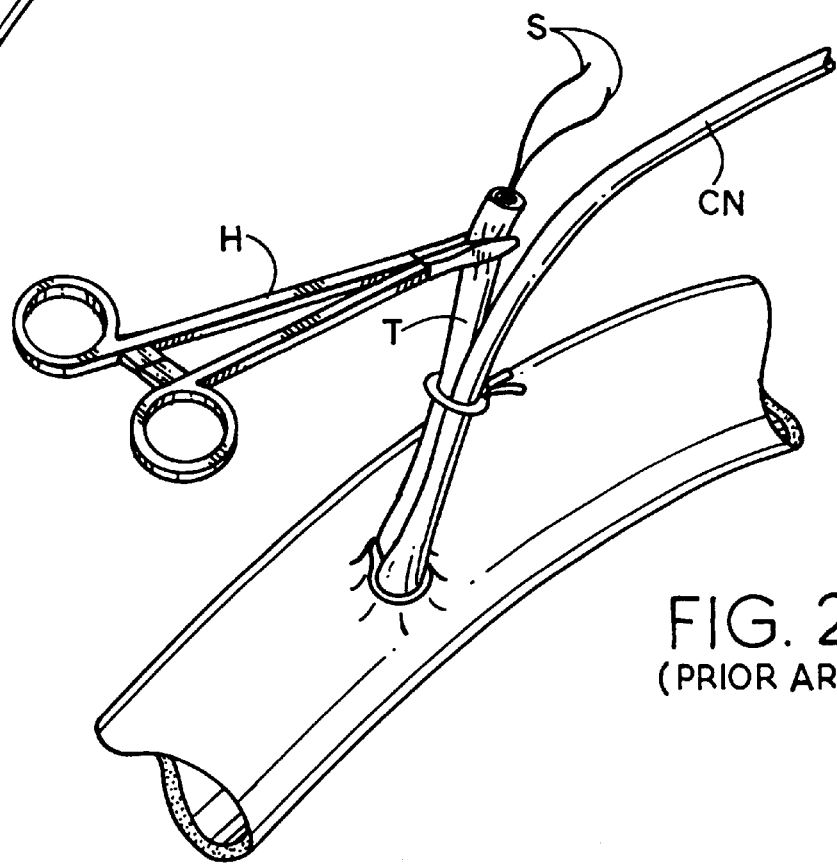
FIG. 2A shows a prior art cannula penetrating a great vessel where the purse-string sutures are used to tighten the tissue around the cannula tip with a garret created by a rubber hose.
Figure 3:
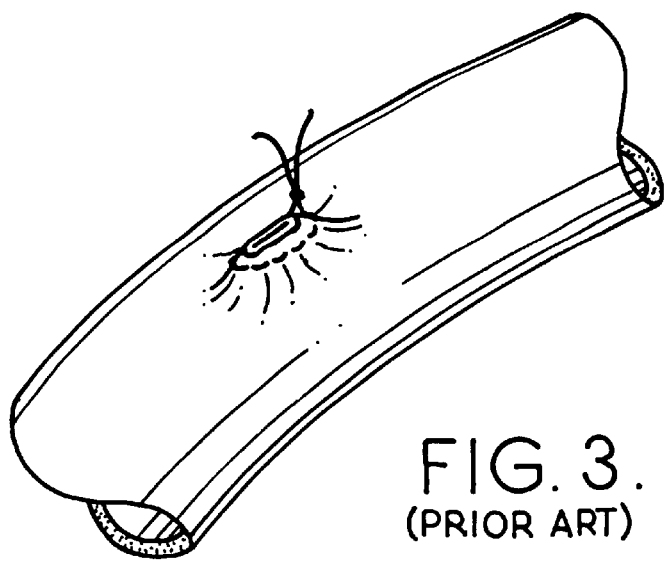
FIG. 3 shows a prior art sutured cannula port after closure.
Figure 2C:
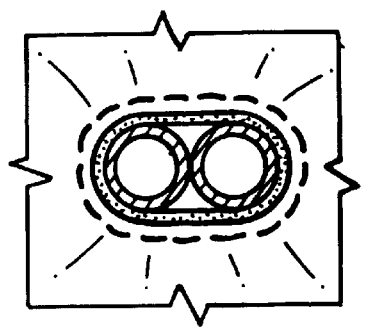
FIG. 2C shows a top view of a leak area between two cannulas.
Figure 2B:
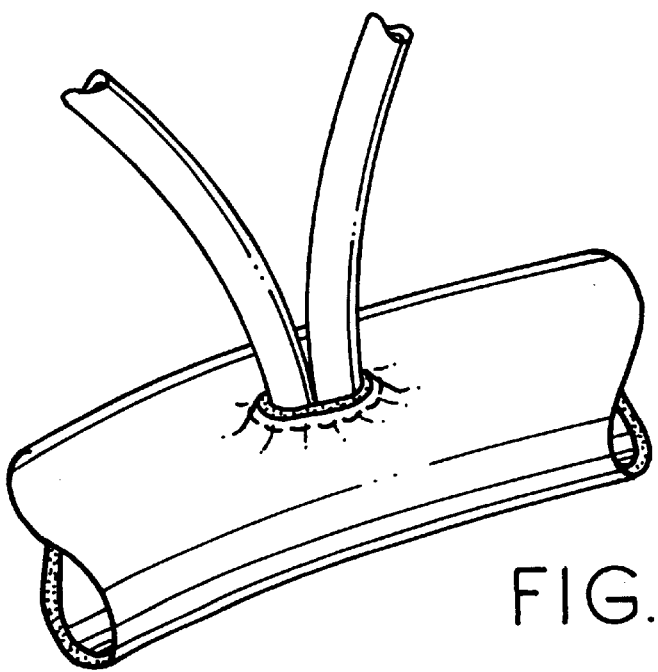
FIG. 2B shows a leak area between two cannulas.

Upon removal of the cannula, tube T is taken off purse-string suture ends E, cannula CN is removed from the vessel and the sutures are pulled tight which puckers and gathers the surrounding tissue and tightens off the access incision and closes it as shown in FIG. 3.

This is a rather lengthy procedure and in addition, tightening the suture effectively eliminates the tissue from the inside of the purse-string leading to displacement of the tissue outside the purse-string and distortion of the vessel wall and the creation of undue stress on the tissue.

Figure 4:
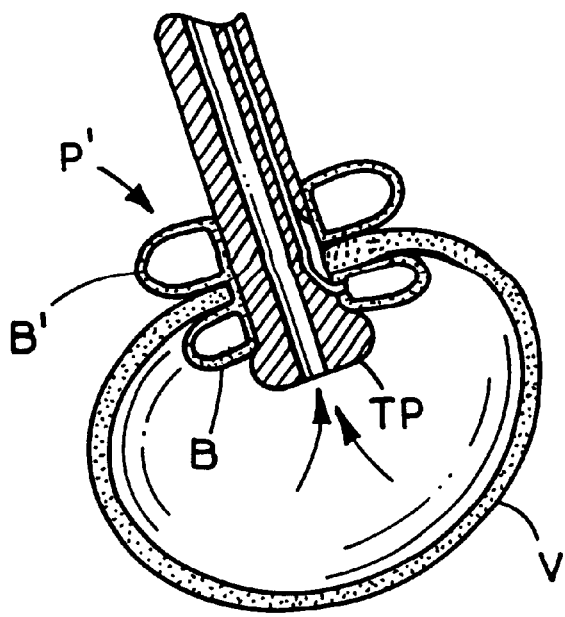
FIG. 4 shows a prior art double balloon cannula access device.

An alternate prior art port P' is shown in FIG. 4. Port P' includes a cannula tip having two torroidal shaped balloons B and B'. Proximal balloon B' is inflated first and the cannula tip TP is inserted through the incision in the vessel wall and then distal balloon B is inflated to effect a seal and pinch the vessel wall between the two balloons thereby sealing off that area to blood flow. Port P' has the advantage of sealing against the vessel wall but leaves the problem of closing the cannulation incision once the procedure is completed. The problem of closing the incision was discussed above.

Figure 5:
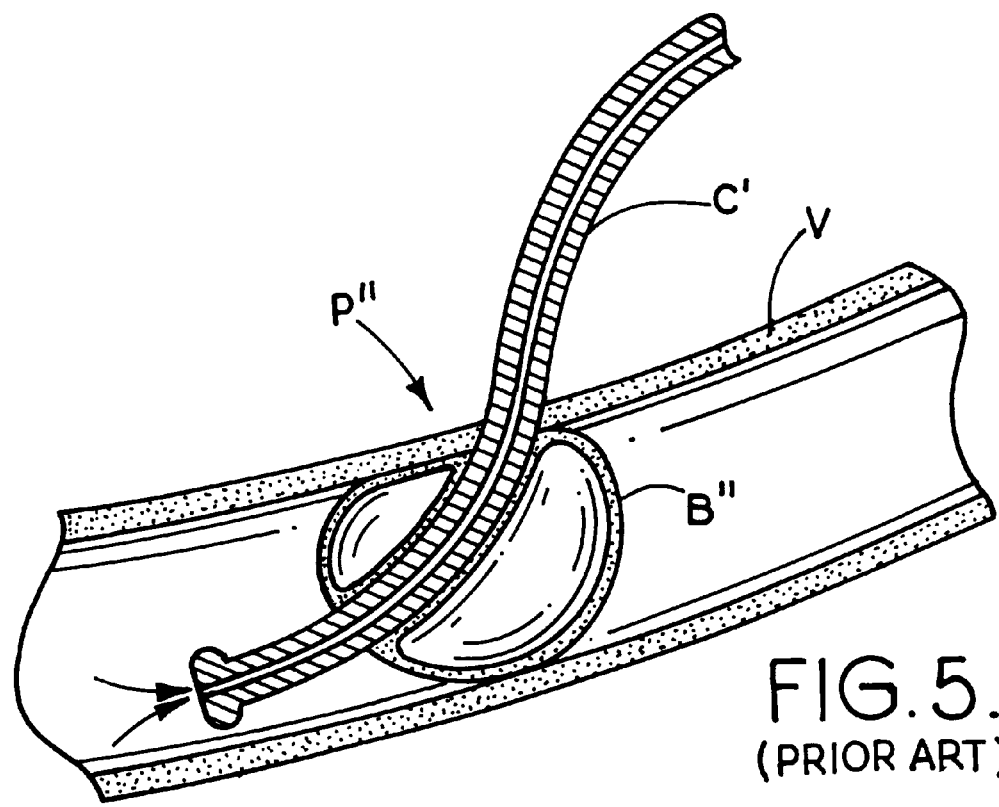
FIG. 5 shows a single balloon prior art cannula access device.

Another type of prior art port P" is shown in FIG. 5 and includes a single balloon B" which occludes the entire cross-sectional area of the vessel. Blood flow is diverted through the center of catheter tube C'. The device shown in FIG. 5 also has the problem of closing the incision after completion of the procedure.

Figure 6:
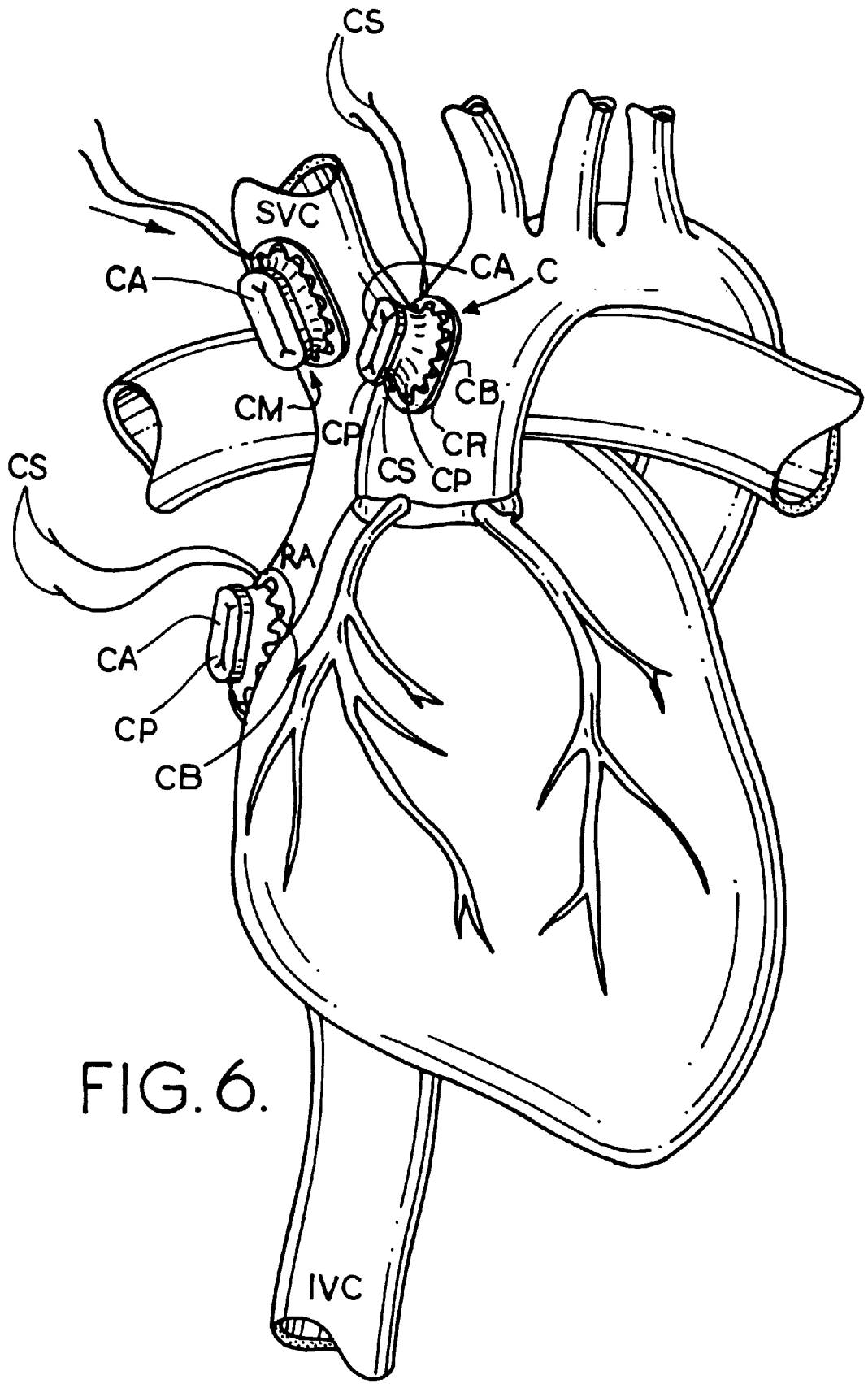
FIG. 6 shows cannula ports of the present invention on great vessels.

Referring to FIG. 6, several rapid access cannulation ports embodying the present invention are shown. The ports can be located anywhere and on any anatomical structure, but for the sake of disclosure, ports are shown on the aorta, the superior vena cava and on the right atrium.

Installation of a port of the present invention is similar to the installation of the rings in the incorporated disclosures. These disclosures are incorporated herein by reference; however, the disclosure will be briefly summarized here for the sake of clarity.

Figure 7:
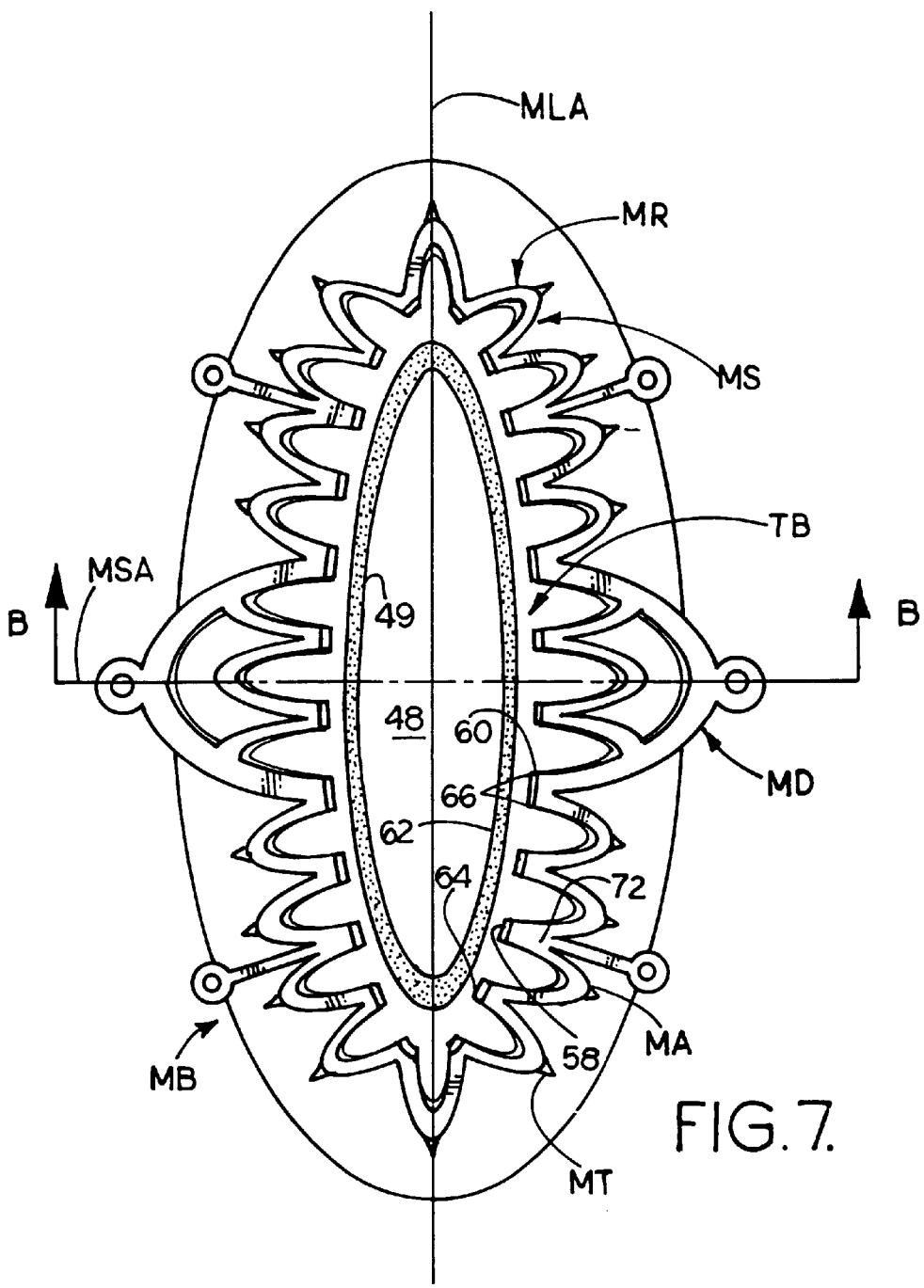
FIG. 7 shows a top view of the malleable ring disclosed in the incorporated disclosures.
Figure 8A:
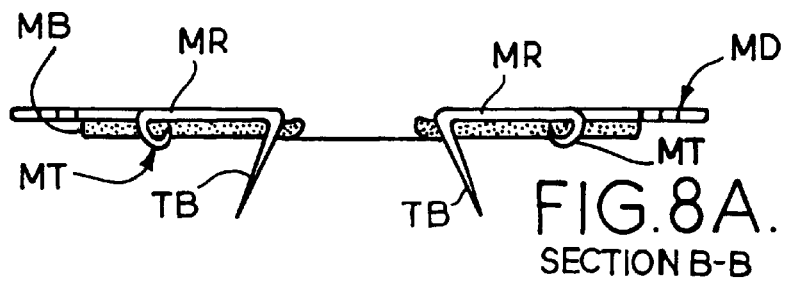
FIG. 8A is a view taken along line B—B of FIG. 7.
Figure 8B:
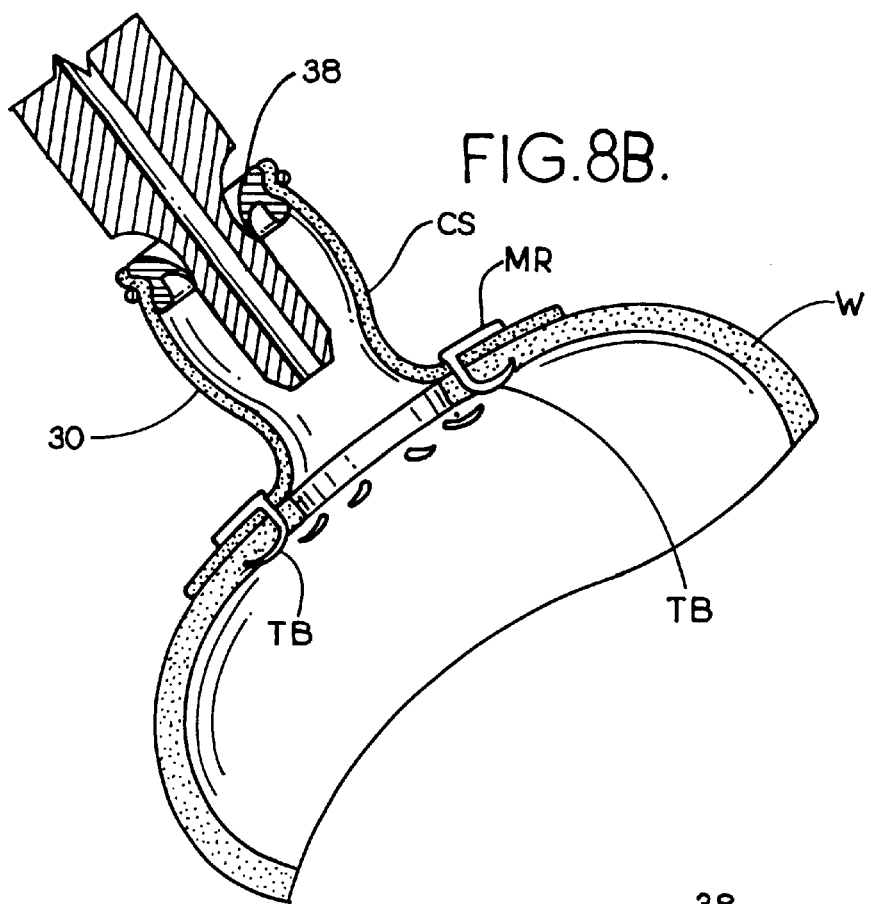
FIG. 8B is a cross-sectional view of the malleable ring of FIG. 7, showing a Dacron sleeve of the present invention fastened in place on an anatomical structure to provide access to the interior of the structure.
Figure 8C:
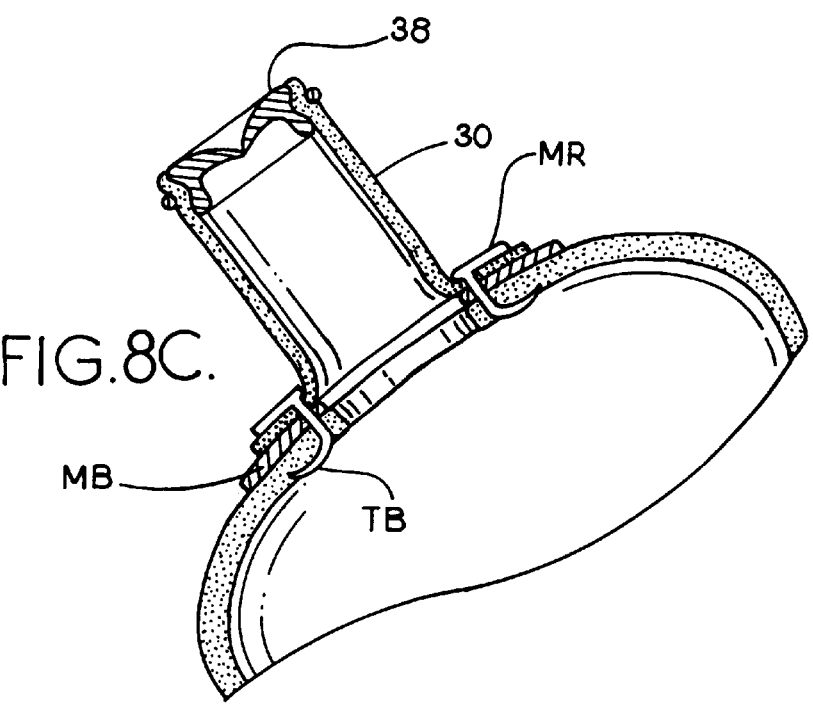
FIG. 8C is a cross-sectional view of the malleable ring of FIG. 7, showing a silicone sleeve of the present invention fastened in place on an anatomical structure through a hemostatic medium to provide access to the interior of the structure.
Figure 9A:
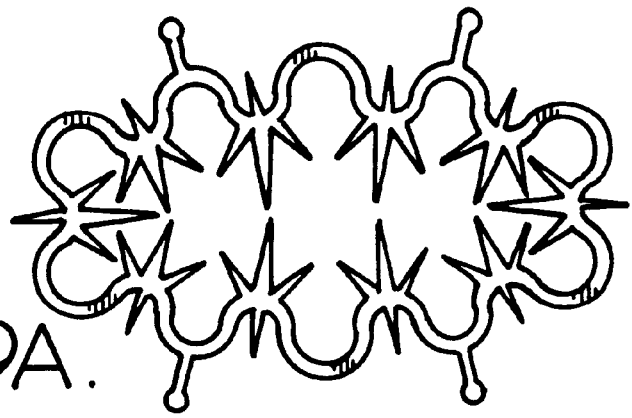
FIGS. 9A–9F show alternative forms of the malleable ring.
Figure 9B:
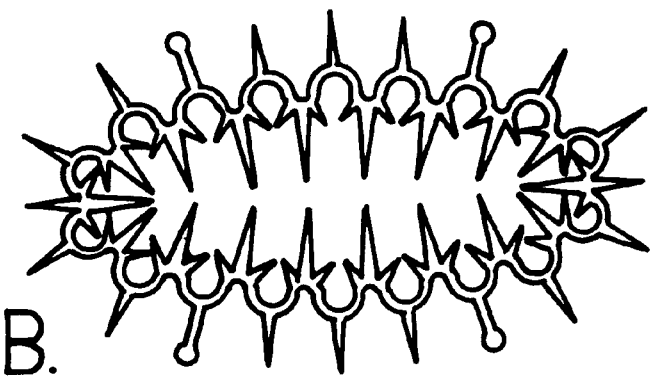
Figure 9C:
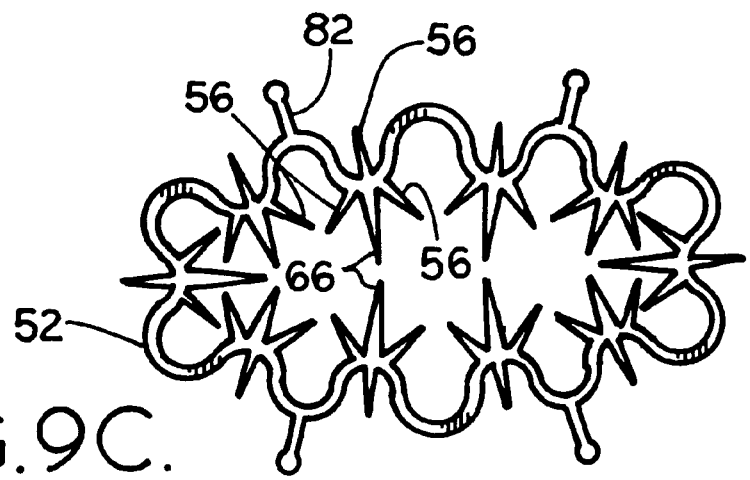
Figure 9D:
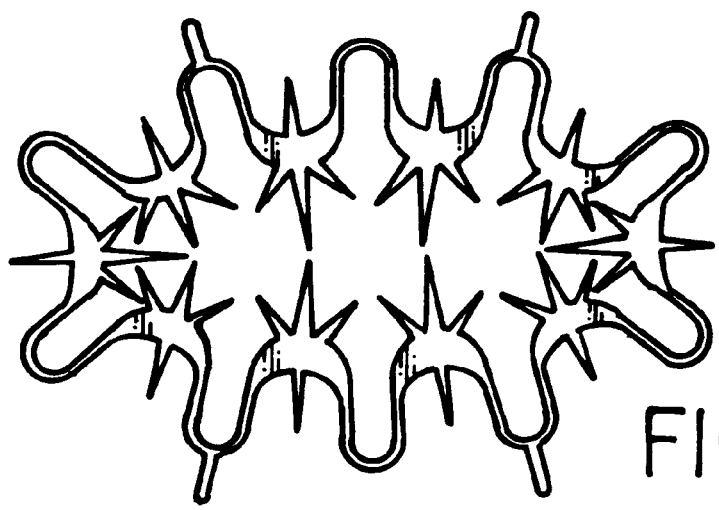
Figure 9E:
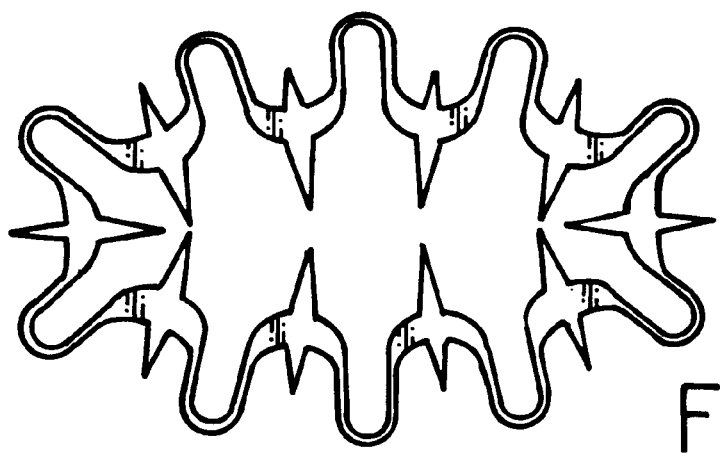
Figure 9F:
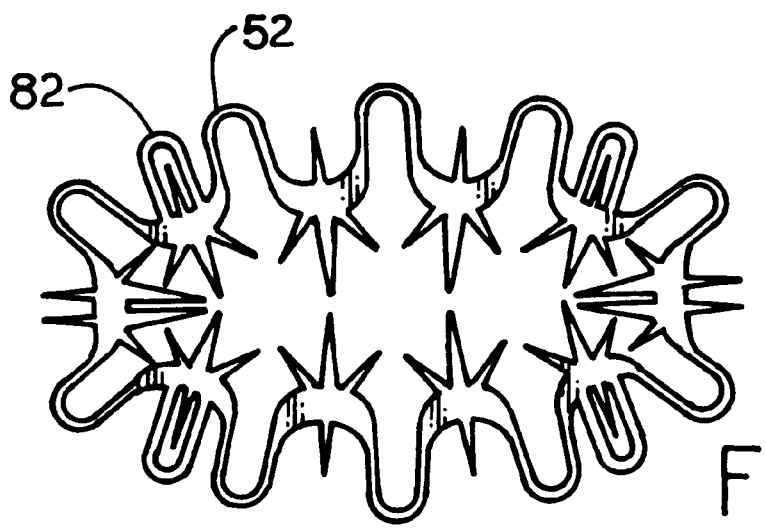

Referring to FIGS. 7, 8A, 8B and 8C which correspond to the figures in the incorporated disclosures, it is seen that a malleable ring MR includes a plurality of arcuate sections MS with apexes MA on which tines MT are located. The tines are shaped as shown in FIG. 8A to engage the vessel wall. Ring MR is malleable and has little material memory which permits it to be deformed from the oval configuration shown in FIG. 7 with a short axis MSA being a fraction of long axis MLA into a more circular configuration in which the short axis is a significant percentage of the long axis, and to then retain that shape until-mechanically deformed again back toward the FIG. 7 configuration. A base MB of hemostatic medium is seen in FIGS. 7, 8A and 8C and also shown and discussed in the incorporated disclosure. Tissue retaining pins TB are also attached to the ring. Docking elements MD are also included on the ring. Engaging and manipulating docking elements MD with an appropriate tool, such as described in the incorporated disclosure, permits the ring to be located, placed and configured on the vessel or organ wall. Another tool will also be disclosed below. Other ring configurations are shown in FIGS. 9A through 9F.

While a hemostatic medium is shown in FIG. 7, 8A and 8C, such a medium might not be necessary in all cases. For example, in FIG. 8B the ring is shown attaching a sleeve 30 to the wall W of an anatomical structure, without the interposition of a hemostatic medium. In this case the sleeve is fabricated of a woven Dacron material having an outside surface of the same material used for vascular grafts (i.e., the same as a hemostatic medium). FIG. 8C shows a sleeve 30 fabricated of silicone with a hemostatic medium MB sandwiched between a mounting flange on the sleeve and the wall W of the anatomical structure.

Broadly, referring to FIG. 6, the present invention is embodied in an apparatus for establishing access to the interior of an anatomical structure such as an internal organ, a blood vessel or the like. The apparatus C, in one form, comprises a malleable ring CR such as ring MR and if desired a base CB similar to base MB, flexible sleeve CS having a distal end CD, a proximal end CP and an access element CA fixed to the distal end of the sleeve. A plurality of fasteners such as fastener TB and tines such as tine MT are fixed to the malleable ring adjacent to the proximal end of the sleeve, with each fastener located and shaped to extend through a wall of the structure for fixing the sleeve to the structure adjacent to an incision in the wall of the structure and to extend back toward the incision. Apparatus C also includes closure structure CM on the sleeve for closing the sleeve and approximating the edges of the wall of the anatomical structure adjacent to the incision to promote healing after an operation has been completed. Closure structure CM includes a suture CS. Suture CS is tightened to close the sleeve and approximate the wall edges into a healing location after completion of the surgical procedure and a one-way valve can be positioned in the sleeve through which a cannula or other instrument can extend into the interior of the structure. The flexible sleeve is hollow and thus is one form of a passage through which access to the interior of the structure is gained. Tightening suture CS seals the sleeve. The suture serves as one form of a means for sealably closing the sleeve and the passage therethrough.

Placement of the rapid access port is indicated in FIGS. 10–15 with respect to a vessel V. A small incision is defined through wall W of vessel V where it is desired to position a cannula to define edges 10 of the vessel wall. An anvil 12 is button holed into the interior lumen of the vessel. The anvil is discussed in the incorporated disclosure and includes a reverse fastener guiding surface 14 on each side of a handle 16 for engaging and turning fasteners TB to form those fasteners after they have been forced through wall W. The formed fasteners in combination with tines MT, mount malleable ring MR on wall W. As discussed in the incorporated disclosure, fasteners TB are formed inward toward the incision and toward each other to pull edges 10 of wall W into a proper position during the fastener forming process.

Figure 10:
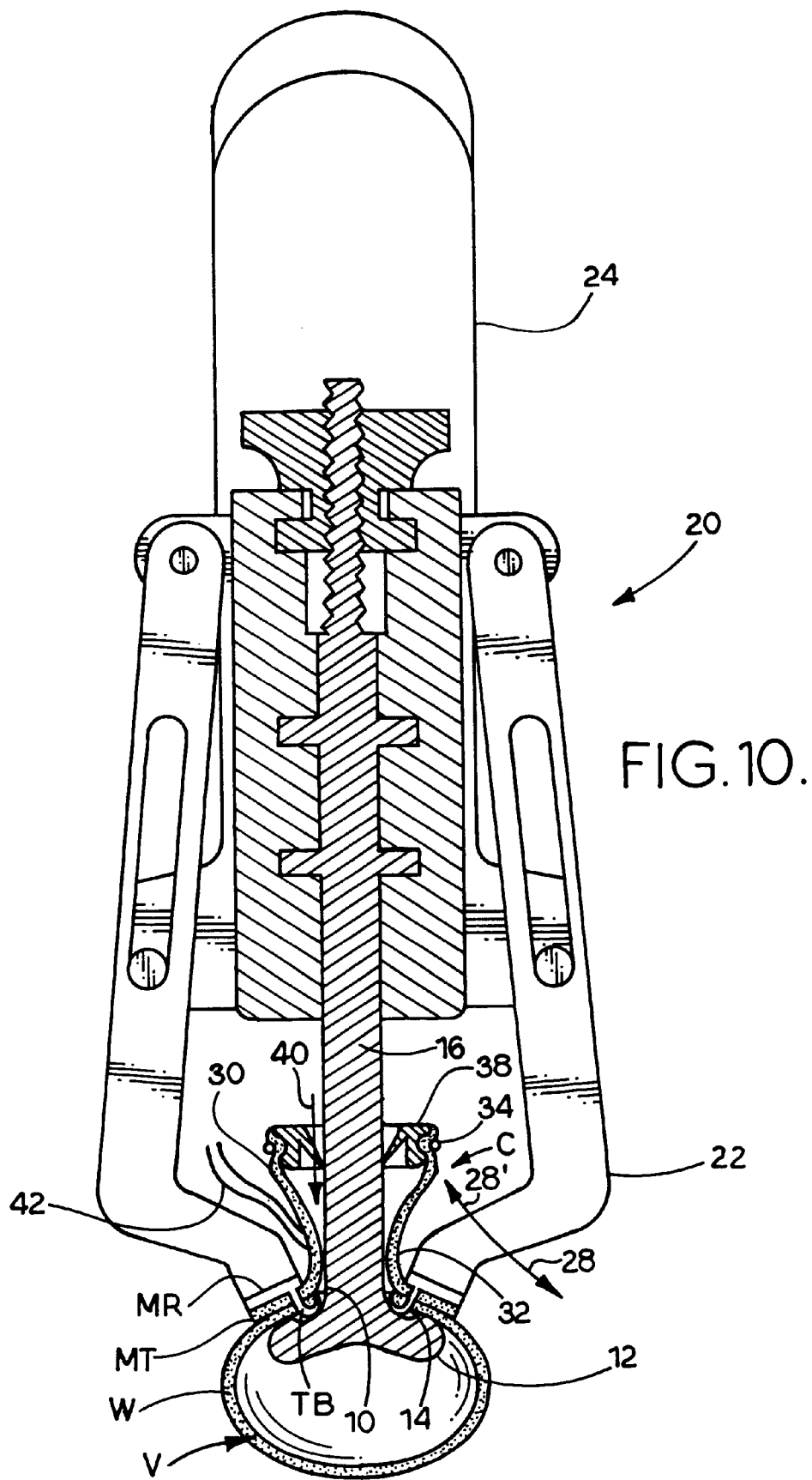
FIG. 10 is a sectional view of an installation tool crimping the cannula port onto a vessel.
Figure 11:
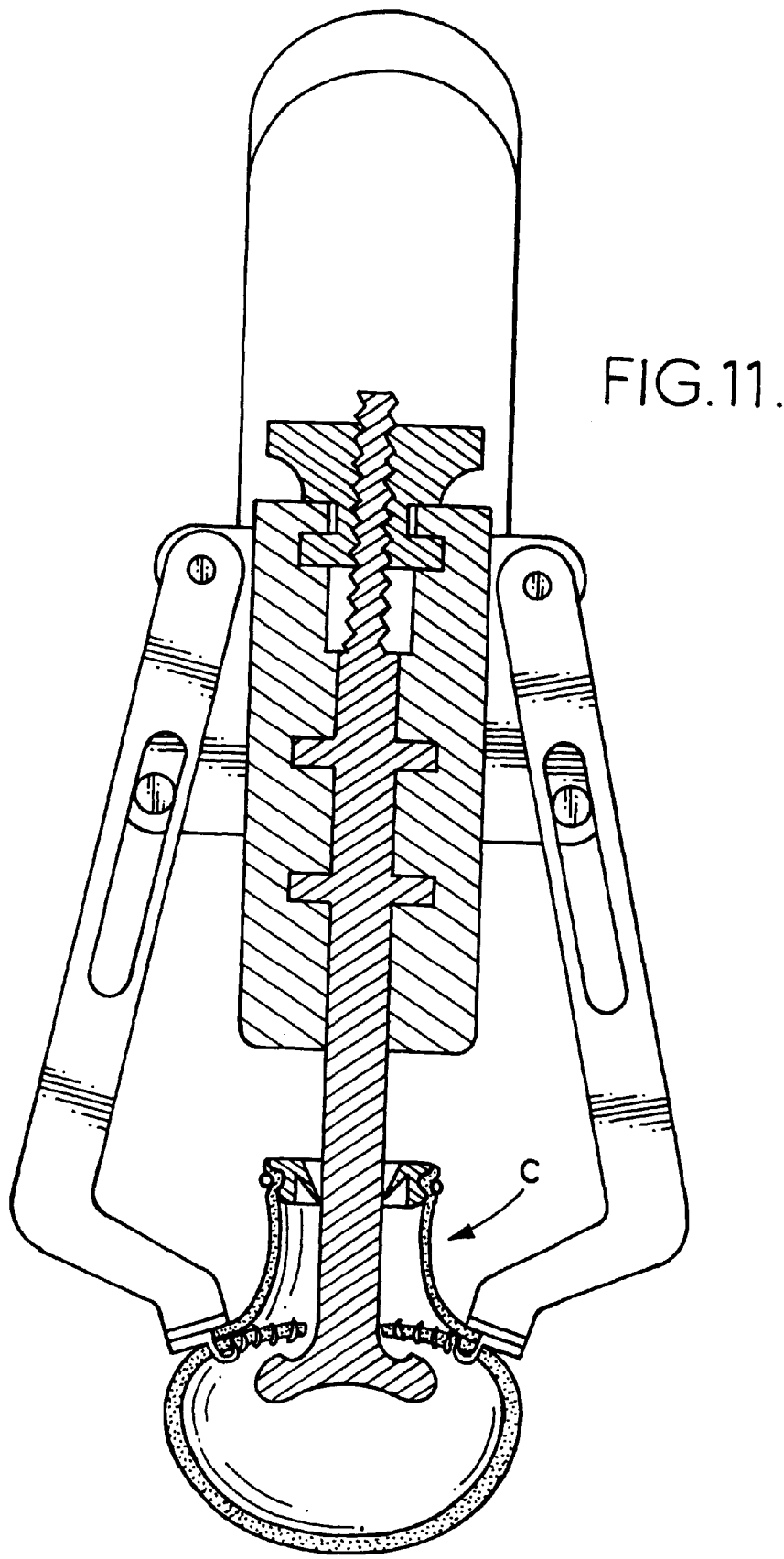
FIG. 11 shows the crimping tool opening up the cross-sectional area allowing an anvil to be pulled out from within the organ or vessel.

As indicated in FIGS. 10 and 11, a tool 20 includes arms 22 pivotally connected to a handle 24 to move arm ends 26 in directions 28 and 28' after releasably engaging docking elements MD. After engagement between arms 22 and the ring, the arms and the anvil are moved toward each other to form the ring and the fasteners. Once the ring is secured to the vessel wall, arms 22 are manipulated to open the ring as indicated in FIG. 11 and the anvil is removed from the vessel.

Still referring to FIGS. 10 and 11, it can be seen that apparatus C includes a sleeve 30 to which the malleable frame is attached at the proximal end of the sleeve. The sleeve is hourglass shaped from a neck portion 32 adjacent to the frame element to a mouth portion 34 on a distal end of the sleeve. A snap ring 36 is located on the sleeve adjacent to the mouth portion on the outside surface of the sleeve, and a one-way valve 38, in one form of the invention, is positioned inside the body adjacent to the mount portion and is held in place by the snap ring. One-way valve 38 opens into the sleeve in direction 40. However, valve 38 is flexible enough to permit anvil 12 to move past it in a direction opposite to direction 40 without permanently damaging that valve. Valve 38 prevents fluid flow out of vessel V and is constructed out of very pliable material such as silicone rubber and is preferably a duckbill type valve. Closing sutures 42 are threaded into sleeve 30 and extend out of the patient. Sutures 42 are threaded into sleeve 30 in a manner which will close neck portion 32 when the sutures are tightened. A tissue cutter such as described in the incorporated disclosures is included to complete the formation of the incision and can be included on tool 20. Sleeve 30 is flexible whereby movement of the distal end thereof is not transferred to wall W. This isolates a cannula attached to the sleeve from the tissue.

As shown in FIG. 12, after the anvil has been removed, a cannula tip 44 can be inserted through sleeve 30 to establish fluid communication between the interior 46 of vessel V and a device associated with cannula via cannula tubing 48. Blood can flow to the cannula via tip 50 as indicated by arrows, such as arrow 52. However, with the cannula removed, blood cannot flow out of the port as indicated in FIG. 13 because the one-way valve prevents such outward flow. In this manner, a rapid access port 54 is formed on vessel V.

As described with reference to FIGS. 8A and 8B, sleeve 30 can be constructed of biological fabric such as Dacron, or a monolithic silicon material. The one-way valve may be connected to the sleeve by any suitable means including glue, overmolding or the like. Manufacturing methods such as insert molding could also be used to combine the valve element with the malleable ring.

Closure sutures 42 are pre-installed in the sleeve adjacent to neck portion 32. The closure sutures may be either in a purse-string arrangement around the periphery of the neck portion or the sutures can be zigzagged from opposite walls so as to be within the sleeve. The sutures provide rapid closure of the incision once the cannula is removed. The incision should also be closed so that the intima come together in an edge to edge configuration with a minimum of puckering or no puckering or bunching of the tissue when healing is desired. The closure suture is arranged in sleeve 30 so that tightening of the suture pulls neck portion together and pulls the walls of the vessel adjacent to the incision together to close off the port and bring the wall of the vessel into healing contact. In course of pulling the walls of the sleeve together, the suture also serves to deform and move the sides of the ring MR toward each other.

Figure 14:
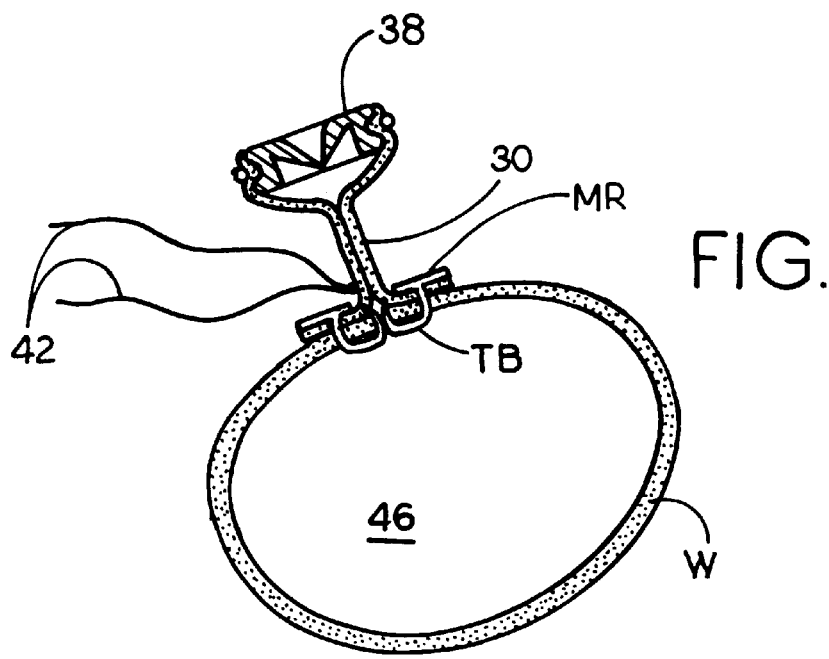
FIG. 14 shows the drawstring sutures or the pulling sutures pulling the vessel walls back together for closure.
Figure 15:
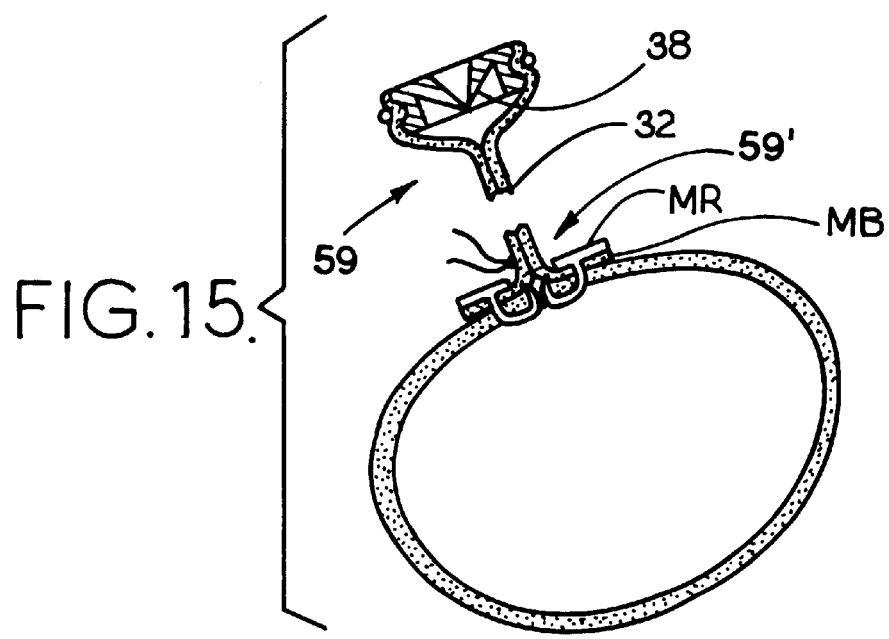
FIG. 15 shows the cutting off of the valve.

Access port 54 after removal of the cannula is shown in FIG. 13. One-way valve 38 is shut to prevent excessive loss of blood during removal of the cannula. Once the cannula has been removed, purse-string sutures 42 are tightened to approximate the edges of the ring which brings tissue edges 10 into contact to permit natural healing. The sleeve material remains at the outer edges of the vessel wall to restrict any blood loss and to provide an area for hemostasis. FIG. 14 shows the access port in a closed configuration. Once sutures 42 have been tightened and the vessel walls have been approximated, the sleeve is cut near neck portion 32 using scissors or the like. Removed portion 59 of the sleeve has valve 38 therein and is discarded as indicated in FIG. 15 leaving portion 59' of the sleeve with malleable frame, or ring, MR on the vessel. This completes the rapid access and closure procedure.

Figure 16:
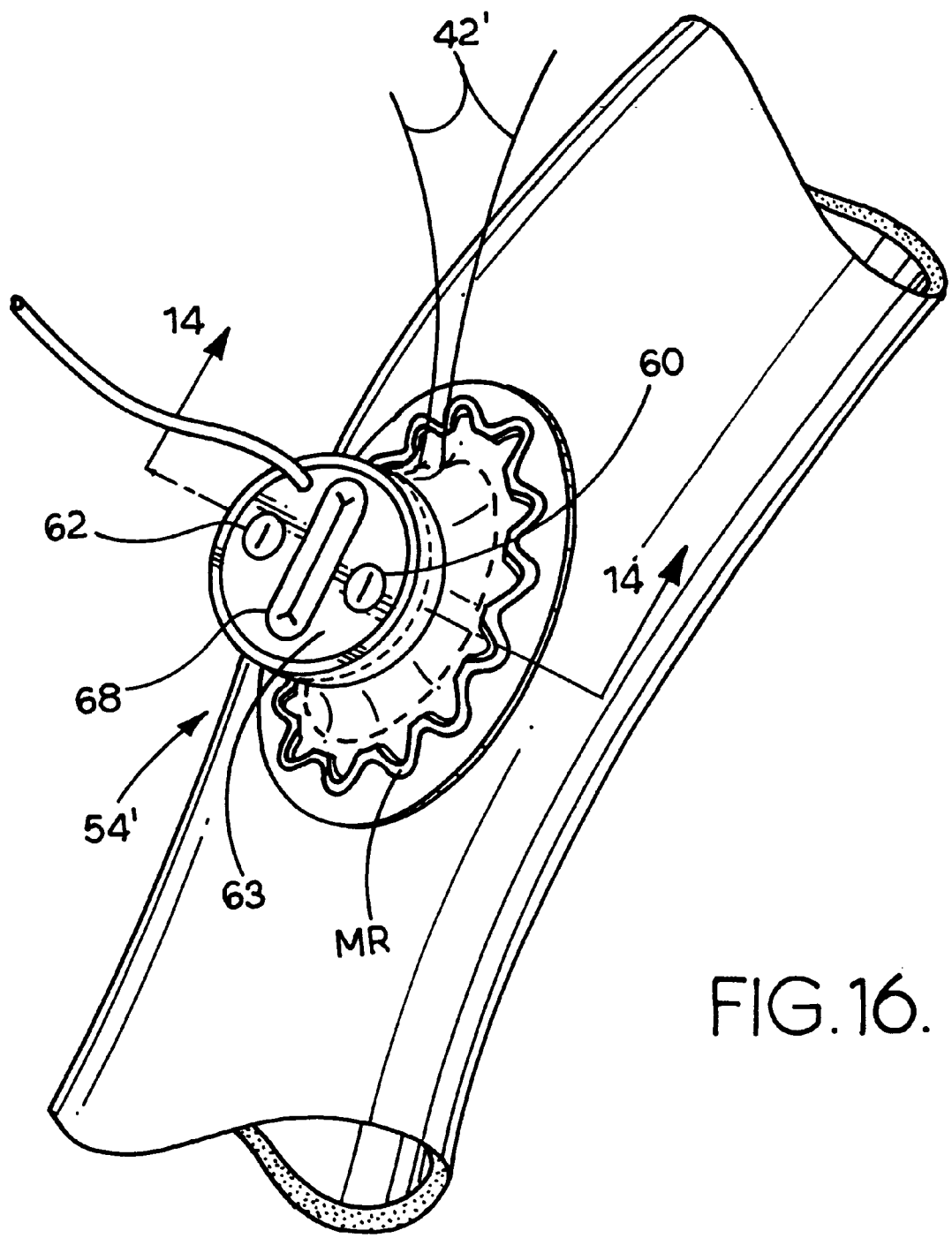
FIG. 16 is a perspective view of a multiple port access device.
Figure 17:
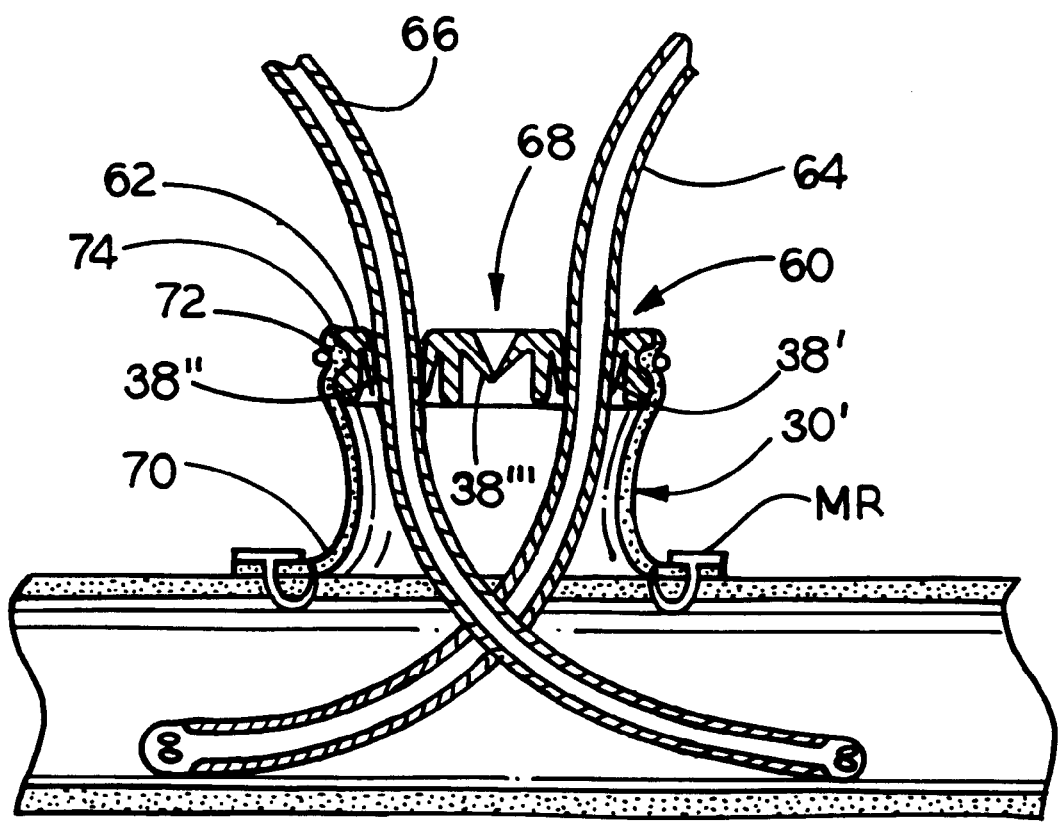
FIG. 17 is a sectional view of a multiple port access device with access cannulas.

The above description is directed to a single cannula and a vessel. However, as noted above, any internal organ can be cannulated in this manner, and more than one cannula can be used or a cannula in combination with other elements can be used. These alternatives are illustrated in FIGS. 16 et seq. A port device 54' includes two ports 60 and 62 defined in a top panel 63 and which can accept cannulas, such as cannulas 64 and 66 through one-way valves 38' and 38" mounted in sleeve 30'. A third port, port 68, is also defined through the top panel 63 and includes a one-way valve 38'". One cannula can be an air vent if desired. A fabric sleeve 70 is formed of suitable fabric, such as double velour fabric or the like, defines body 30' and a malleable frame MB is attached to the cuff for the purpose and function described above with reference to port 54. As shown in FIG. 17, a seal or reinforcing element 72 is located adjacent to mouth portion 74 of sleeve 30'. Sutures 42' are threaded into sleeve 30' in the manner discussed above for closing the sleeve as discussed above after removal of the cannulas or other elements. Tightening of the sutures draws the edges of the vessel together as discussed above.

Referring to FIGS. 18–24, a brief description of how the access device of the present invention can be used will be presented with reference to a heart valve replacement procedure. In order to perform a valve replacement procedure, the surgeon must make a large incision transverse across the ascending aorta to gain access to the interior lumen of the aorta. This access incision is usually between four and eight centimeters in length. The size of the access and closure port is substantially larger than the size of the anastomosis device disclosed in the incorporated application, but works on the same principles using a malleable retaining ring with staple legs on the ring.

For an aortic valve replacement procedure, the patient is placed on bypass and the aorta is cross-clamped. The surgeon then makes a small incision transverse to the aorta. An anvil, which can be shaped to conform to the internal curvature of the vessel, is inserted through the small incision and is button-holed into the interior lumen. The driving device has the sleeve, ring, tines and fasteners attached thereto and is attached to the anvil. The tool is activated to form the fasteners and attach the ring and sleeve to the wall of the structure with the fasteners being crimped as shown in FIG. 10. After the fasteners are crimped, a knife blade on the tool is operated to complete the incision and allow the anvil to be removed after the incision is opened by manipulation of the tool arms as discussed above. This procedure fastens the access port device to the aorta. Once the access port device is fastened to the aorta, the malleable ring can be manipulated as desired using forceps or the tool 20.

In the case of an aortatomy, the superior or top edge ME (see FIG. 23) of the closure ring is deflected inward toward the inside lumen 46 of the vessel while lower or inferior edge IE is pulled outward. This opens the incision and allows full access to the aortic valve area 80 to perform the valve surgery.

Figure 18:
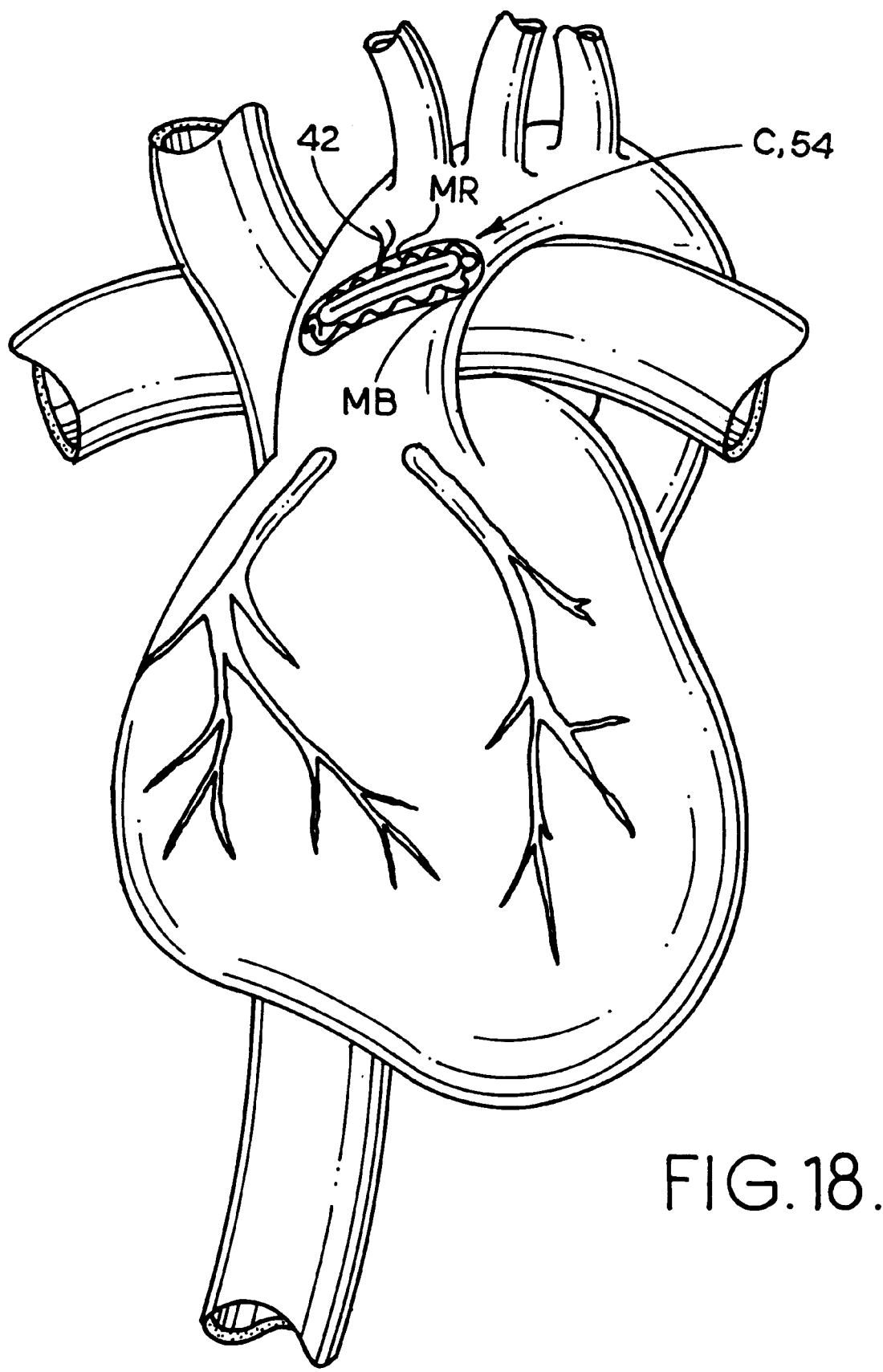
FIG. 18 shows the access and closure device on the ascending aorta.
Figure 20:
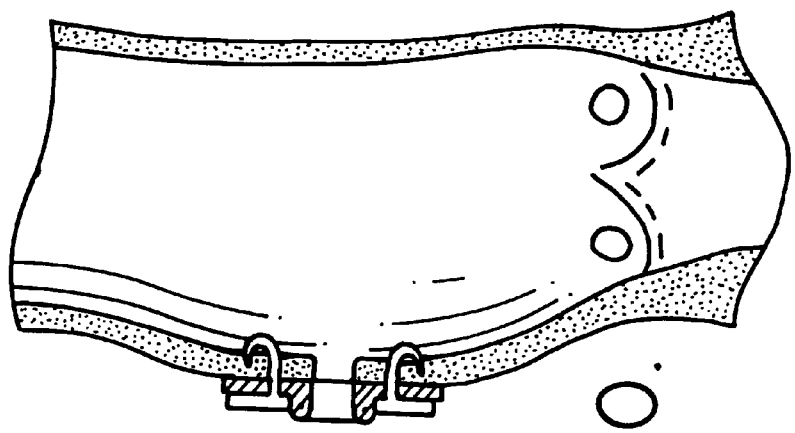
FIG. 20 shows the access and closure port cinched in place on the aorta.
Figure 19:
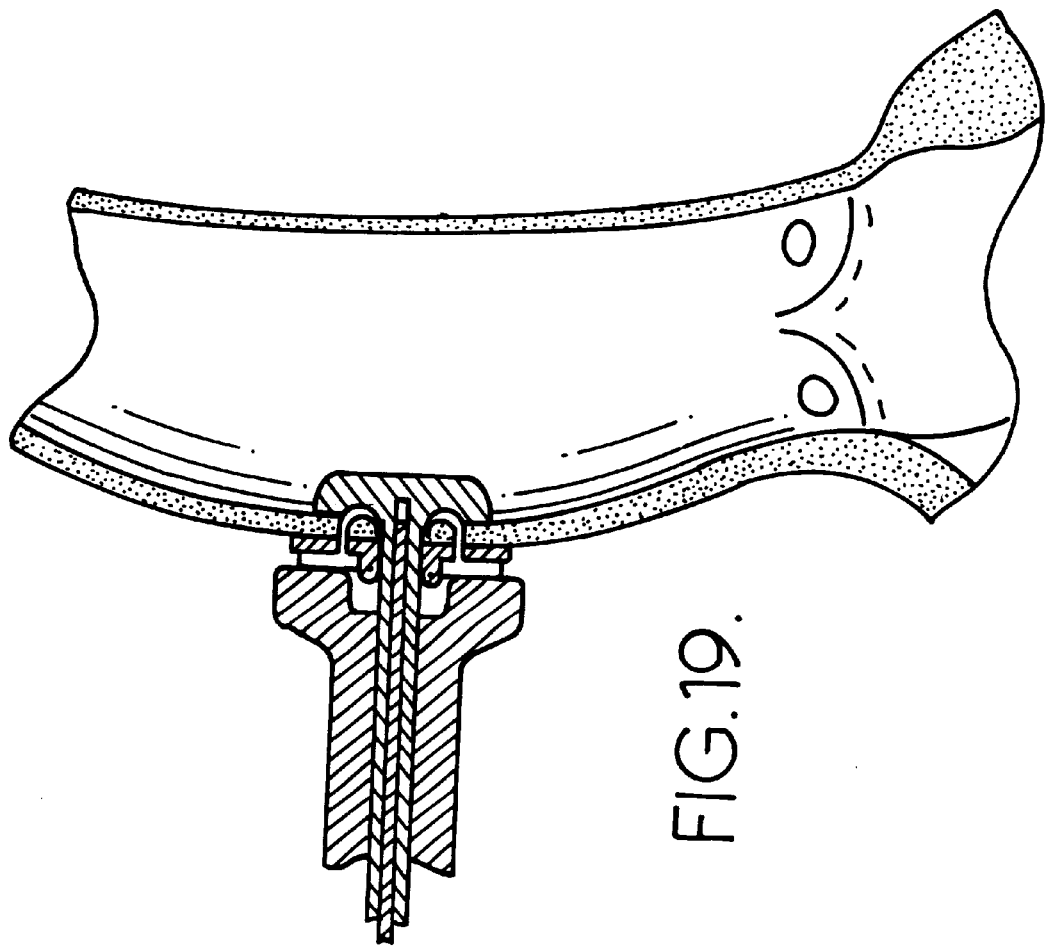
FIG. 19 shows a cross-section of the aorta with the anvil and driver installing an access and closure port.
Figure 23:
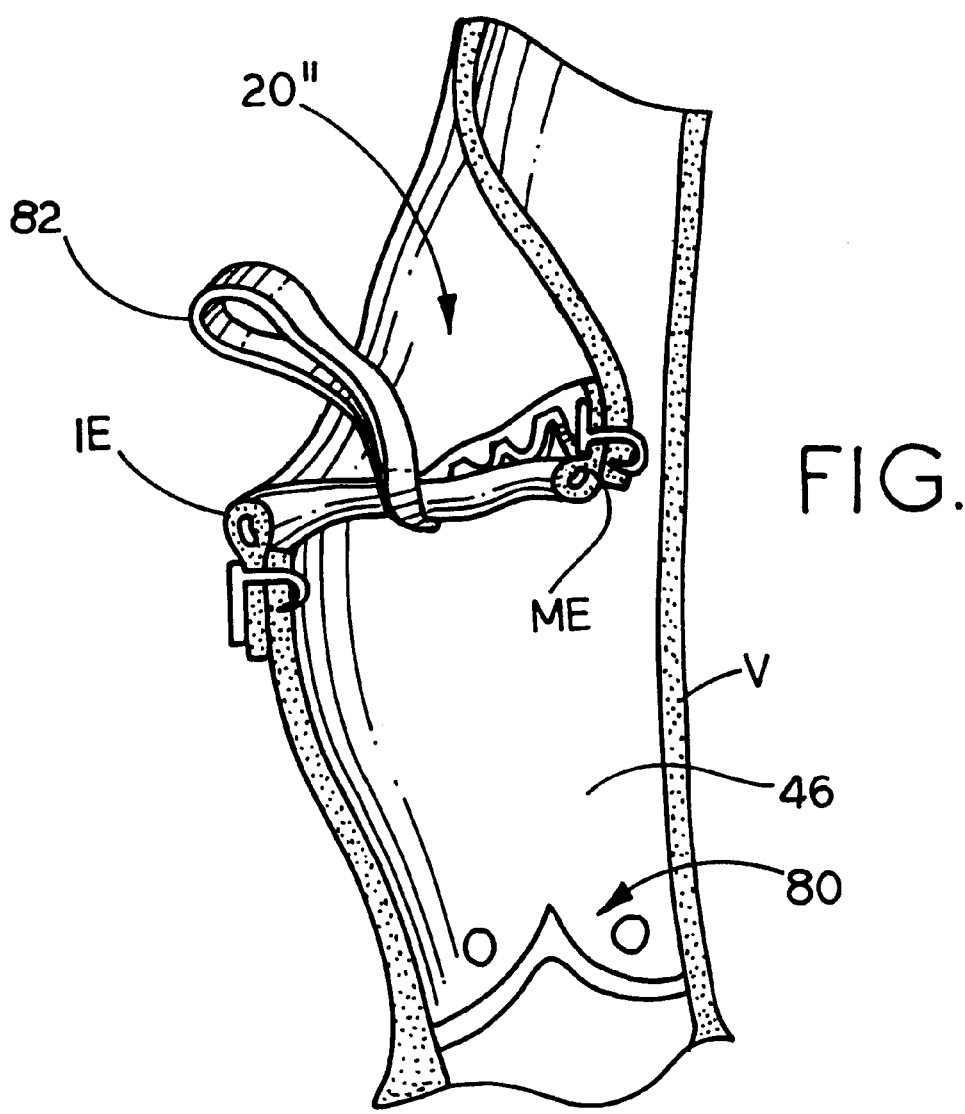
FIG. 23 is a cross-sectional view of the aorta showing the device after the metal ring has been deformed to hold the aorta open to allow access to the valve.
Figure 24:
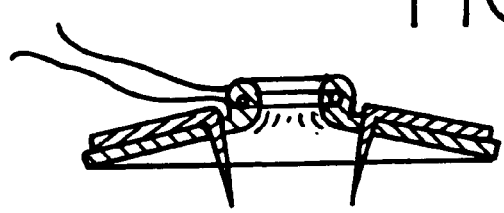
FIG. 24 is a sectional view of the access and closure device prior to being attached to an aorta.

With the malleable fastener ring attached to the sleeve, the edges of the vessel are formed into a shape which allows entry and exit into the aorta which would otherwise have to be maintained with retractors. Device 20" is shown in FIG. 23 as including a bulldog clip 82 for maintaining the sutures 42' out of the way. Device 20" maintains the open access to the valve region 80 without the use of external retractors which may get in the way and restrict access of tools used to complete the valve procedure. The closed device is shown in FIG. 18. This same device can be used to gain access and close any lumenal structure to which the surgeon needs access. In cardiothoracic there is a need to gain access to the right atrium, left atrium and the ventricles. This access device can be used in each instance.

After surgery is complete, the malleable ring is flexed by means of forceps or other suitable tool and formed so that the edges of the lumen come back together. The bulldog clips which have held the closure sutures out of the way during surgery, are removed using suitable tools such as forceps or the like. This allows the sutures which zigzag across the opening (see FIG. 21) of the cuff to be pulled tight like the laces of a shoe. This brings the edges of the aortic vessel wall into approximation and allows for proper healing of the vessel tissue. This will be a very fast way to close a large incision without the need to place sutures in an area that has restricted access due to a minimally invasive surgery technique. With the sleeve on the outside pulled tightly together with the closure sutures, the leakage of blood is minimized, if not totally eliminated, and a hemostatic support can be provided.

Figure 25:
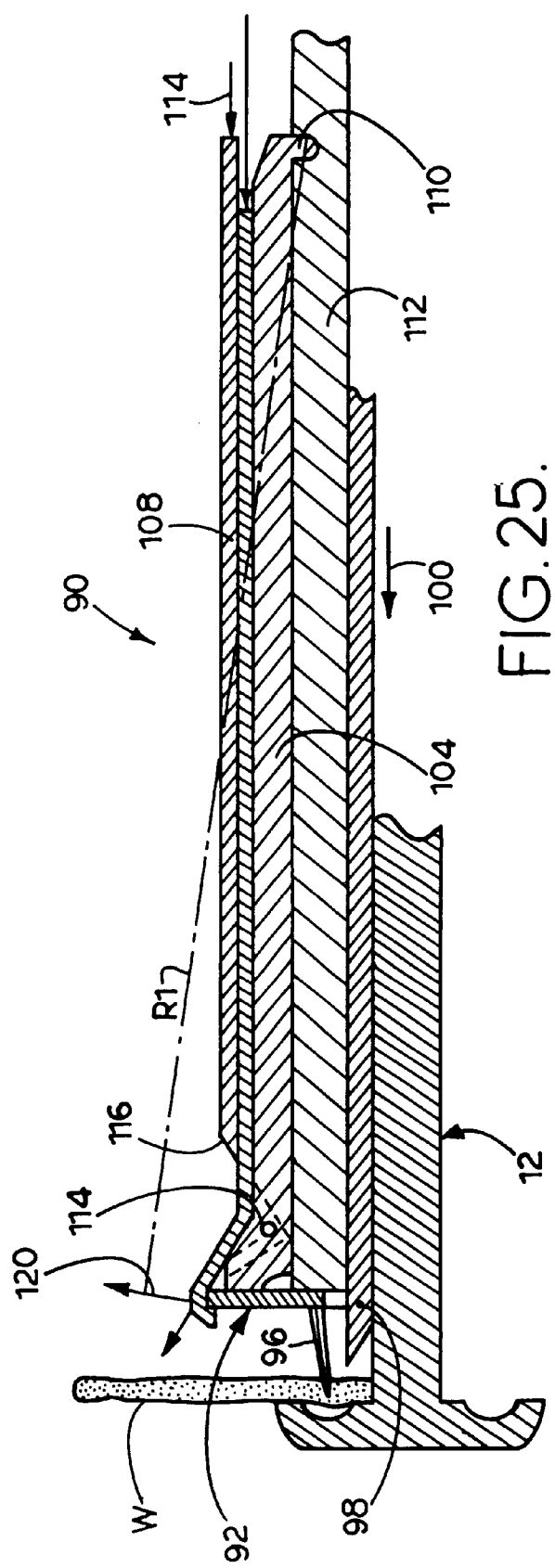
FIG. 25 shows a cutaway elevational view of a tool used to manipulate the ring of the device of the present invention.

A tool 90 suitable for manipulating the cuff and the malleable ring is illustrated in FIGS. 25 and 26. Tool 90 is used in conjunction with a malleable -ring 92 having a docking element 94 and fasteners 96. Ring 92 is used in connection with the above-discussed sleeve but such elements are omitted from FIGS. 25 and 26 to more clearly show tool 90 and its cooperation with the access port device. Tool 90 also works in conjunction with an anvil 12 and a tissue cutter 98 which is operated by a handle (not shown in FIGS. 25 and 26) located outside the patient. Any suitable mechanism such as a knob and screw mechanism, can be used to drive cutter 98 toward the anvil head in direction 100 to cut tissue 102 after fasteners 96 have been formed.

Tool 90 includes a spreader cam 104 having a docking engaging head 106 on a distal end thereof and is located inside a sleeve 108 and includes a pivot connection 110 on a proximal end thereof connecting the proximal end to a driver 112. A cam pin 114 is fixed to the spreader arm and slidably engages a canted cam surface 116. Sleeve 108 is movably mounted on driver 112 to move in direction 114 by means of any suitable mechanism such as hand-operated lever or trigger located outside the patient's body on a handle. When sleeve 108 is moved in direction 114, cam surface 116 slidably engages cam pin 114 and drives that cam pin outward in direction 120 while spreader cam 104 pivots outward in direction 120 due to its pivotal connection 110 to driver 112. A ring retainer 122 has a hook 124 on a distal end thereof for releasably engaging a corresponding notch 126 defined in docking element 94. Projection tabs 128 are located on head 106 to releasably engage corresponding notches 130 and 132 on docking element 94. With tabs engaged in notches 130 and 132 and hook 124 engaged with the docking element via notch 126, movement of head 106 is transferred to the ring 92 via the docking element 94.

Driver 112 is also connected to an operating mechanism in a handle to move in direction 100 when desired. Movement of driver 112 in direction 100 forces fastener 96 through the vessel tissue and into engagement with reverse fastener guiding surface 14 whereby the fastener is formed.

In this manner, the fasteners are forced through the tissue and formed. Then the ring 92 can be configured and manipulated as desired to permit the anvil to be removed as discussed above. Tool 90 can also be used to close the device into the configuration shown in FIGS. 14, 15 and 18 by engaging the ring with heads 106 and operating the spreader cams as discussed above. The heads 106 are engaged with the docking elements 94 by friction and can be released from these elements by moving the tool 90 and pulling the heads off of the docking elements.

It is understood that while certain forms of the present invention have been illustrated and described herein, it is not to be limited to the specific forms or arrangements of parts described and shown.

What is claimed is:

1. Apparatus for establishing access to the interior of a hollow anatomical structure, such as a heart or a blood vessel comprising:
   a malleable frame;
   a flexible sleeve having a distal end and being fixed to said frame;
   a plurality of fasteners on said frame, each fastener having a prong located and shaped to extend through a wall of the anatomical structure for fixing said sleeve to the structure adjacent to an incision therein for communication with the interior of the structure through the incision; and
   closure means for closing said sleeve and approximating the wall of the anatomical structure adjacent to the incision to promote healing of the vessel after an operation has been completed.

2. The apparatus defined in claim 1 wherein said closure means comprises a suture in said sleeve.

3. The apparatus defined in claim 1 wherein said frame is annular and has an inner edge and an outer edge and each fastener has a proximal end fixed to said frame and being shaped so the frame inner edge is positioned between the fastener distal and proximal ends.

4. The apparatus defined in claim 1 further comprising means on said sleeve for releasably attaching said sleeve to a placement tool.

5. The apparatus defined in claim 1 further comprising a reinforcing element on said sleeve adjacent to the distal end of said sleeve.

6. The apparatus defined in claim 1 further comprising a hemostatic medium on said sleeve.

7. The apparatus defined in claim 1 further comprising a one-way valve mounted on said sleeve.

8. The apparatus defined in claim 7 wherein said valve includes an access port.

9. The apparatus defined in claim 8 further comprising a plurality of access ports included in the valve.

10. Apparatus for establishing restricted access to a hollow anatomical structure during surgery comprising:
    a sleeve;
    a docking element on said sleeve for attaching an element such as a cannula to said sleeve;
    means for mounting said sleeve on the hollow anatomical structure; and
    a one-way valve on said sleeve.

11. The apparatus defined in claim 10 further comprising means for closing said sleeve after completion of a surgical procedure.

12. The apparatus defined in claim 11 further comprising means on said sleeve for holding one portion of the anatomical structure in approximation with another portion of the anatomical structure.

13. Apparatus for establishing restricted access to a hollow anatomical structure during surgery comprising:
    a malleable frame for mounting on an anatomical structure adjacent to an incision through a wall of the structure;
    means on said frame for creating a sealable passage between the interior of the structure and the exterior of the structure through said frame; and
    means for sealably closing said passage.

14. The apparatus defined in claim 13 wherein said sealable passage includes a flexible sleeve.

15. The apparatus defined in claim 10 wherein said sealable passage is normally closed.

16. Apparatus for establishing a resealable access into the interior of an anatomical structure through a wall of the structure during a surgical procedure comprising:
    a malleable frame mounted on a wall of the structure adjacent to an incision through the wall, said frame being movable from a first configuration holding the incision open to a second configuration closing the incision;
    a sleeve secured to the wall around the incision; and
    means on said sleeve for closing the incision.

17. The apparatus defined in claim 16 wherein said sleeve includes a docking port for connecting an instrument such as a cannula or the like to said sleeve.

18. The apparatus defined in claim 17 wherein said docking port further includes a one-way valve.

19. The apparatus defined in claim 18 wherein said one-way valve includes projections which engage a tip of the instrument.

20. The apparatus defined in claim 18 wherein said sleeve further includes a plurality of docking ports.

21. The apparatus defined in claim 17 wherein said docking port further includes a seal.

22. The apparatus defined in claim 16 wherein said means for closing said sleeve comprises a suture on said sleeve.

23. The apparatus defined in claim 22 wherein said suture is located inside said malleable frame.

24. The apparatus defined in claim 22 wherein said suture is located outside said malleable frame.

25. The apparatus defined in claim 24 further comprising fasteners and tines on said malleable frame.

26. The apparatus defined in claim 25 further comprising means for attaching a plurality of instruments to said sleeve.

27. A method of cannulating a hollow anatomical structure during surgery comprising:
    establishing access to the interior of an internal anatomical structure;
    creating a sealable passage between the interior of the structure and the exterior of the structure;
    performing a surgical procedure in the interior of the structure through the passage; and
    after completing the surgical procedure sealing the passage with a tissue manipulating malleable frame.

28. The method defined in claim 27 further including holding one portion of the structure in approximation with another portion of the structure after sealing the passage using a tissue manipulating malleable frame.

29. The method defined in claim 27 wherein the step of establishing access includes defining an incision in the structure.

30. The method defined in claim 29 wherein the sealable passage includes a one-way valve and the step of creating a sealable valve.

31. The method defined in claim 29 further including attaching a malleable ring to the structure adjacent to the incision.

32. The method defined in claim 31 further including a step of spreading the malleable ring to provide access to the structure through the incision.

33. The method defined in claim 32 wherein the surgical procedure includes cannulating the structure.

34. The method defined in claim 33 wherein the step of sealing the passage includes closing the structure.

35. The method defined in claim 34 wherein the sealable passage includes a sleeve and the step of sealing the passage includes cutting the sleeve.

36. Apparatus for establishing access to the interior of a hollow anatomical structure, such as a heart or a blood vessel comprising:
    a malleable frame;
    a flexible sleeve having a distal end and being fixed to said frame;
    a plurality of fasteners on said frame, each fastener having a prong located and shaped to extend through a wall of the anatomical structure for fixing said sleeve to the structure adjacent to an incision therein for communication with the interior of the structure through the incision; and
    closure structure engaged with said sleeve, said structure being selectively operable to compress the sleeve into a closed condition adjacent to the incision to promote healing of the vessel after an operation has been completed.

37. The apparatus defined in claim 36 wherein the closure structure comprises a suture extending around the sleeve.

38. The apparatus defined in claim 36 wherein said frame is annular and has an inner edge and an outer edge and each fastener has a proximal end fixed to said frame and being shaped so the frame inner edge is positioned between the fastener distal and proximal ends.

39. The apparatus defined in claim 36 further comprising a reinforcing element on said sleeve adjacent to the distal end of said sleeve.

40. The apparatus defined in claim 36 further comprising a hemostatic medium on said sleeve.

41. The apparatus defined in claim 36 further comprising a one-way valve mounted on said sleeve.

42. The apparatus defined in claim 41 wherein said valve includes an access port.

43. The apparatus defined in claim 42 further comprising a plurality of access ports.

44. Apparatus for establishing restricted access to a hollow anatomical structure during surgery comprising:
   a sleeve;
   a docking element on said sleeve for attaching an element such as a cannula to said sleeve;
   fasteners on the sleeve securely engageable with the hollow anatomical structure for mounting said sleeve around an incision in the anatomical structure; and
   a one-way valve on said sleeve.

45. The apparatus defined in claim 44 further comprising closure structure engaged with said sleeve, said closure structure being selectively operable to compress the sleeve into closed condition after completion of a surgical procedure.

46. The apparatus defined in claim 45 further comprising elements on said sleeve engageable with the anatomical structure for holding one portion of the anatomical structure in approximation with another portion of the anatomical structure.

47. Apparatus for establishing restricted access to a hollow anatomical structure during surgery comprising:
   a malleable frame for mounting on an anatomical structure adjacent to an incision through a wall of the structure;
   a passage element having an end peripherally secured to the frame for creating a sealable passage between the interior of the structure and the exterior of the structure through said frame; and
   closure structure engaged with the passage element, said closure structure being selectively operable to close the passage element.

48. The apparatus defined in claim 47 wherein the passage element includes a flexible sleeve.

49. The apparatus defined in claim 47 wherein said sealable passage is normally closed.

50. Apparatus for establishing a resealable access into the interior of an anatomical structure through a wall of the structure during a surgical procedure comprising:
   a malleable frame mounted on a wall of a structure adjacent to an incision through the wall, said frame being movable from a first configuration holding the incision open to a second configuration closing the incision;
   a sleeve secured to the wall around the incision; and
   structure engaged with said sleeve for selectively closing the incision.

51. The apparatus defined in claim 50 wherein the sleeve includes a docking port for connecting an instrument such as a cannula or the like to the sleeve.

52. The apparatus defined in claim 51 wherein said docking port further includes a one-way valve.

53. The apparatus defined in claim 52 wherein said one-way valve includes projections which engage a tip of the instrument.

54. The apparatus defined in claim 52 wherein the sleeve further includes a plurality of docking ports.

55. The apparatus defined in claim 51 wherein said docking port further includes a seal.

56. The apparatus defined in claim 50 wherein the closure structure comprises a suture extending around the sleeve.

57. The apparatus defined in claim 56 wherein the suture is located inside said malleabe frame.

58. The apparatus defined in claim 56 wherein the suture is located outside said malleable frame.

59. The apparatus defined in claim 58 further comprising fasteners and tines on said malleable frame.

60. The apparatus defined in claim 59 further comprising means for attaching a plurality of instruments to said sleeve.

* * * * *